(12) United States Patent
Sholev et al.

(10) Patent No.: US 9,801,633 B2
(45) Date of Patent: Oct. 31, 2017

(54) SURGICAL FASTENING DEVICE AND METHOD

(71) Applicant: Artack Medical (2013) Ltd., Maccabim-Reut (IL)

(72) Inventors: Mordehai Sholev, Moshav Amikam (IL); Gilad Lavi, Rishon-LeZion (IL)

(73) Assignee: Artack Medical (2013) Ltd., Maccabim-Reut (IL)

( * ) Notice: Subject to any disclaimer, the term of this patent is extended or adjusted under 35 U.S.C. 154(b) by 280 days.

(21) Appl. No.: 14/347,299

(22) PCT Filed: Sep. 24, 2012

(86) PCT No.: PCT/IB2012/055079
§ 371 (c)(1),
(2) Date: Mar. 26, 2014

(87) PCT Pub. No.: WO2013/046115
PCT Pub. Date: Apr. 4, 2013

(65) Prior Publication Data
US 2014/0243855 A1    Aug. 28, 2014

Related U.S. Application Data

(60) Provisional application No. 61/539,013, filed on Sep. 26, 2011.

(51) Int. Cl.
*A61B 17/10* (2006.01)
*A61B 17/064* (2006.01)
*A61B 17/068* (2006.01)

(52) U.S. Cl.
CPC ............ *A61B 17/10* (2013.01); *A61B 17/064* (2013.01); *A61B 17/068* (2013.01); *A61B 2017/0647* (2013.01); *A61B 2017/0648* (2013.01)

(58) Field of Classification Search
CPC .... A61B 2017/0646; A61B 2017/0647; A61B 2017/0648; A61B 2017/0649;
(Continued)

(56) References Cited

U.S. PATENT DOCUMENTS 5,582,616 A    12/1996  Bolduc et al.
5,810,882 A     9/1998  Bolduc et al.
(Continued)

FOREIGN PATENT DOCUMENTS

EP    1382302     1/2004
EP    1990014    11/2008
(Continued)

OTHER PUBLICATIONS

Translation Dated Dec. 27, 2015 of Notification of Office Action and Search Report dated Dec. 7, 2015 From the State Intellectual Property Office of the People's Republic of China Re. Application No. 201280057915.5.

(Continued)

*Primary Examiner* — Jonathan Miles
*Assistant Examiner* — Kankindi Rwego

(57) ABSTRACT

A fastening device, comprising an inner tube comprising a proximal end and a distal end and at least one fastener positioned within the inner tube and adapted to advance linearly towards the distal end of the inner tube, and an advancing element which converts rotational motion to linear pushing force on the fastener. In some embodiments of the invention, at least one fastener is adapted to not rotate at all or to rotate at a rate not necessarily the same as any other fasteners or any other elements during linear advancement.

30 Claims, 36 Drawing Sheets

(58) Field of Classification Search
CPC . A61B 17/0409; A61B 17/064; A61B 17/068; A61B 17/07207; A61B 17/3417; A61B 17/3468; A61B 17/349; A61B 17/10; A61B 2017/07235; A61B 17/8883; A61B 17/8886; A61B 17/8891; B25B 23/04; B25B 23/08; B25B 23/10; B25B 19/00
USPC .......................................................... 606/104
See application file for complete search history.

(56) References Cited

U.S. PATENT DOCUMENTS

| | | | |
|---|---|---|---|
| 5,824,008 | A | 10/1998 | Bolduc et al. |
| 5,830,221 | A | 11/1998 | Stein et al. |
| 5,964,772 | A | 10/1999 | Bolduc et al. |
| 6,296,656 | B1 | 10/2001 | Bolduc et al. |
| 6,562,051 | B1 | 5/2003 | Bolduc et al. |
| 6,837,893 | B2 | 1/2005 | Miller |
| 6,884,248 | B2 | 4/2005 | Bolduc et al. |
| 7,011,668 | B2 | 3/2006 | Sancoff et al. |
| 7,037,315 | B2 | 5/2006 | Sancoff et al. |
| 7,131,978 | B2 | 11/2006 | Sancoff et al. |
| 7,131,979 | B2 | 11/2006 | DiCarlo et al. |
| 7,131,980 | B1 | 11/2006 | Field et al. |
| 7,655,020 | B2 | 2/2010 | Wenzler et al. |
| 7,666,194 | B2 | 2/2010 | Field et al. |
| 7,670,362 | B2 | 3/2010 | Zergiebel |
| 7,722,610 | B2 | 5/2010 | Viola et al. |
| 7,758,612 | B2 | 7/2010 | Shipp |
| 7,862,573 | B2 | 1/2011 | Darois et al. |
| 7,866,526 | B2 | 1/2011 | Green et al. |
| 7,867,252 | B2 | 1/2011 | Criscuolo et al. |
| 7,931,660 | B2 | 4/2011 | Aranyi et al. |
| 2002/0058967 | A1* | 5/2002 | Jervis .................. A61B 17/064 606/213 |
| 2003/0105473 | A1 | 6/2003 | Miller |
| 2004/0106925 | A1 | 6/2004 | Culbert |
| 2004/0243139 | A1* | 12/2004 | Lewis .................. A61B 17/862 606/104 |
| 2008/0097523 | A1 | 4/2008 | Bolduc et al. |
| 2008/0277450 | A1* | 11/2008 | Dudai .................. A61B 17/068 227/179.1 |
| 2011/0071578 | A1 | 3/2011 | Colesanti et al. |

FOREIGN PATENT DOCUMENTS

| | | |
|---|---|---|
| EP | 2260775 | 12/2010 |
| EP | 2263559 | 12/2010 |
| WO | WO 00/28902 | 5/2000 |
| WO | WO 02/17771 | 3/2002 |
| WO | WO 03/103507 | 12/2003 |
| WO | WO 2004/112841 | 12/2004 |
| WO | WO 2008/010948 | 1/2008 |
| WO | WO 2011/008257 | 1/2011 |
| WO | WO 2011/092692 | 8/2011 |
| WO | WO 2013/046115 | 4/2013 |

OTHER PUBLICATIONS

Notification of Office Action and Search Report dated Dec. 7, 2015 From the State Intellectual Property Office of the People's Republic of China Re. Application No. 201280057915.5.
International Preliminary Report on Patentability dated Jun. 19, 2014 From the International Preliminary Examining Authority Re. Application No. PCT/IB2012/055079.
International Search Report and the Written Opinion dated Jan. 17, 2013 From the International Searching Authority Re. Application No. PCT/IB2012/055079.
Written Opinion dated Nov. 19, 2013 From the International Preliminary Examining Authority Re. Application No. PCT/IB2012/055079.
Notification of Office Action and Search Report dated Aug. 8, 2016 From the State Intellectual Property Office of the People's Republic of China Re. Application No. 201280057915.5 and Its Translation Into English.
Patent Examination Report dated May 11, 2016 From the Australian Government, IP Australia Re. Application No. 2012313955.

* cited by examiner

SURGICAL FASTENING DEVICE AND METHOD

RELATED APPLICATIONS

This application is a National Phase of PCT Patent Application No. PCT/IB2012/055079 having International filing date of Sep. 24, 2012, which claims the benefit of priority under 35 USC §119(e) of U.S. Provisional Patent Application No. 61/539,013 filed on Sep. 26, 2011. The contents of the above applications are all incorporated by reference as if fully set forth herein in their entirety.

FIELD AND BACKGROUND OF THE INVENTION

The present invention, in some embodiments thereof, relates to a surgical instrument and, more particularly, but not exclusively, to a surgical fastening device.

U.S. Pat. No. 7,670,362 to Zergiebel discloses an applicator for applying an absorbable screw fastener to tissue, the applicator comprising an outer tube housing a cylindrical drive, a pilot in the form of a needle, and a plurality of absorbable screw fasteners. The cylindrical drive includes fingers adapted to hold a distal most screw fastener in position for application in the body. The cylindrical drive, pilot and screw fasteners rotate in order to advance a fastener into body tissue. In some embodiments, the cylindrical drive and pilot also advance distally until the pilot extends out of the distal end of the outer tube housing.

US 2011/0071578 discloses a surgical fastener system including a tube having an inner bore with an internal threaded portion, housing a plurality of fasteners having a throughbore with a non-circular cross section portion. The fasteners engage with a splined mandrel that passes through the throughbore of the fasteners and rotates the fasteners relative to the mandrel to move at least one of the fasteners along the mandrel's longitudinal axis. A distal end of the mandrel may be inserted into a material such as a tissue, prosthetic or other, and a fastener may be deployed from the distal end of the mandrel while the distal end is positioned in the material. In some embodiments, a pusher element is provided adapted to engage with the mandrel for rotation with the mandrel and engage with the internal threaded portion of the inner bore for urging fasteners to move distally on the mandrel.

Additional background art includes U.S. Pat. No. 7,666,194 to Field et al., U.S. Pat. No. 7,011,668 to Sancoff, et al., U.S. Pat. No. 7,037,315 to Sancoff et al., U.S. Pat. No. 7,131,979 to DiCarlo et al., U.S. Pat. No. 7,131,978 to Sancoff et al., U.S. Pat. No. 6,837,893 to Miller, U.S. Pat. No. 7,131,980 to Field et al., U.S. Pat. No. 7,862,573 to Darois et al., WO 2008/010948 by Colesanti et al., WO 2011/008257 by Felix, U.S. Pat. No. 7,866,526 to Green et al., EP 2263559 by Bolduc et al., U.S. Pat. No. 5,582,616 to Bolduc et al., U.S. Pat. No. 5,810,882 to Bolduc et al., U.S. Pat. No. 5,824,008 to Bolduc et al., U.S. Pat. No. 5,964,772 to Bolduc et al., U.S. Pat. No. 6,296,656 to Bolduc et al., U.S. Pat. No. 6,562,051 to Bolduc et al., U.S. Pat. No. 6,884,248 to Bolduc et al., US 2008/0097523 to Bolduc et al., EP 1382302 by Bolduc et al., U.S. Pat. No. 5,830,221 by Stein et al., WO 2000/028902 by Jervis, U.S. Pat. No. 7,867,252 to Criscuolo et al., U.S. Pat. No. 7,758,612 to Shipp, U.S. Pat. No. 7,722,610 to Viola et al., U.S. Pat. No. 7,931,660 to Aranyi et al., EP 2260775 by Aranyi and U.S. Pat. No. 7,655,020 to Wenzler.

SUMMARY OF THE INVENTION

An aspect of some embodiments of the present invention relates to a surgical fastening device adapted to both push tacks and rotate screws into the body.

An aspect of some embodiments of the present invention relates to a surgical fastening device adapted to pierce tacks into body tissue without rotating the tacks, by applying rotational force to the fastening device.

An aspect of some embodiments of the invention relates to a surgical fastening device including fasteners which move linearly within the device. In some embodiments, at least some fasteners also rotate during linear displacement. In some embodiments, some of the fasteners located within the device may rotate during linear displacement while other fasteners located in the device may move linearly without rotation. In some embodiments at least two fasteners rotate within the device at different rates and/or directions.

An aspect of some embodiments of the invention relates to fasteners adapted to be used with the above described fastening devices.

An aspect of some embodiments of the present invention relates to a surgical fastening device comprising a shaft around which fasteners are positioned, where the movement of the shaft is independent to the movement of the fasteners. In some embodiments, the outer surface of the shaft is smooth.

An aspect of some embodiments of the present invention relates to a surgical fastening device comprising an attachment mechanism for drawing body tissue towards the fastening device and/or aligning the fastening device with respect to the body tissue.

According to an aspect of some embodiments of the present invention there is provided a fastening device, comprising;

an inner tube comprising a proximal end and a distal end;

at least two fasteners positioned within the inner tube and adapted to advance linearly towards the distal end of the inner tube, wherein the at least two fasteners are adapted to rotate at different rates during linear advancement.

According to some embodiments of the invention, at least one fastener does not rotate during linear advancement.

According to some embodiments of the invention, at least one fastener is adapted to rotate in conjunction with the inner tube.

According to some embodiments of the invention, the at least two fasteners include at least one screw and at least one tack.

According to an aspect of some embodiments of the present invention there is provided a fastening device comprising:

an inner tube comprising a proximal end and a distal end and adapted to rotate along its axis;

at least one fastener positioned within the inner tube and adapted to advance linearly towards the distal end of the inner tube by rotation of the inner tube, without rotating the fastener at the same rate as the inner tube.

According to some embodiments of the invention, the inner tube comprises at least one longitudinal slot along at least a portion of its length and the device further comprising:

an internally threaded outer tube into which the inner tube is inserted; and an advancing element comprising at least one wing, the advancing element positioned within the inner tube such that the threads of the at least one wing protrude out of the at least one slot and are threaded in the inner threads of the outer tube, wherein rotation of the inner tube causes the threaded wing to advance along the inner threads of the outer tube and thereby to advance the advancing element linearly towards the distal end of the inner tube.

According to an aspect of some embodiments of the present invention there is provided A fastening device comprising:

an inner tube having a proximal end and a distal end, the inner tube comprising at least one longitudinal slot along at least a portion of its length;

an internally threaded outer tube into which the inner tube is inserted;

an advancing element comprising at least one wing, the advancing element positioned within the inner tube such that the threads of the at least one wing protrude out of the at least one slot and are threaded in the inner threads of the outer tube; and a fastener positioned within the inner tube between the advancing element and the distal end of the inner tube;

wherein rotation of the inner tube causes the threaded wing to advance along the inner threads of the outer tube and thereby to advance the advancing element and the fasteners linearly towards the distal end of the inner tube.

According to some embodiments of the invention, the wing does not surround the circumference of the inner tube. According to some embodiments of the invention, the wing surrounds the entire circumference of the inner tube.

According to some embodiments of the invention, the inner tube is connected to a rotary drive mechanism of a surgical device.

According to some embodiments of the invention, the fasteners are positioned between the advancing element and the distal end of the inner tube and wherein rotation of the inner tube causes the advancing element to advance the fasteners linearly towards the distal end of the inner tube.

According to some embodiments of the invention, the outer tube does not move linearly with respect to the inner tube.

According to some embodiments of the invention, the fasteners comprise a base and a piercing element and wherein at least one fastener comprises a cavity in its base for receiving a piercing element of another fastener.

According to some embodiments of the invention, at least two fasteners comprise interlocking elements adapted to connect the fasteners to each other such that the connected fasteners will rotate together.

According to some embodiments of the invention, the fasteners comprise a base and wherein at least one fastener comprises a non-circular shaped base and at least one fastener comprises a circular shaped base.

According to some embodiments of the invention, the inner tube has a non-circular shaped cross-section and wherein at least one fastener comprises a non-circular shaped base having at least one common plane with the non-circular cross-section.

According to some embodiments of the invention, the device further comprises a shaft around which the advancing element and fasteners are fitted and wherein the movement of the shaft is independent of the movement of the fasteners.

According to some embodiments of the invention, the shaft is smooth over at least 50% of its length.

According to some embodiments of the invention, the shaft comprises a sharpened distal end for piercing into body tissue.

According to some embodiments of the invention, the shaft is hollow and includes an inner shaft for protecting the sharpened end from harming body tissue, wherein the inner shaft is adapted to be pushed into the sharpened shaft when pushed against body tissue, thereby revealing the sharpened end.

According to some embodiments of the invention, the device comprises a distal end on which a spring is mounted, the spring surrounding the sharpened end of the shaft, such that when the spring is pressed against body tissue the sharpened end of the shaft is exposed.

According to some embodiments of the invention, the shaft does not move linearly with respect to the inner tube.

According to some embodiments of the invention, the shaft is adapted to move in a linear direction only.

According to an aspect of some embodiments of the present invention there is provided a fastening device, comprising:

a shaft; and at least one fastener adapted to be pierced into body tissue, the fastener comprising bore along its length, wherein the bore is fitted onto the shaft, wherein the fastener is adapted to move independently of the movement of the shaft. According to some embodiments, the shaft slides along inside the bore.

According to some embodiments of the invention, the shaft does not move linearly with respect to the device.

According to some embodiments of the invention, the shaft is adapted to move linearly.

According to some embodiments of the invention, the fastener is adapted to rotate around the shaft.

According to some embodiments of the invention, the shaft is smooth over at least 50% of its length.

According to an aspect of some embodiments of the present invention there is provided a fastening device comprising:

a shaft comprising a threaded end; and at least one fastener adapted to be pierced into body tissue, the fastener comprising a bore along its length, wherein the bore is fitted onto the shaft.

According to some embodiments of the invention, the shaft is adapted to rotate independently of the movement of the fasteners.

According to some embodiments of the invention, the shaft comprises a broadened distal end to prevent unintentional dislodgement of the fasteners from the shaft.

According to some embodiments of the invention, the device further comprises at least two wires having a relaxed state curved shape and forced straight into the device, the wires adapted to be pushed out of the distal end of the device and pierce into body tissue while returning to their relaxed curved shape, thereby clamping into the body tissue.

According to some embodiments of the invention, the wires are threaded through bores in the fasteners.

According to some embodiments of the invention, the wires are threaded through conduits in an outer tube of the device.

According to some embodiments of the invention, the wires are made of nickel titanium.

According to some embodiments of the invention, the fastening device is embodied in a straight distal section of a surgical device.

According to some embodiments of the invention, the fastening device is embodied in a distal section of an articulating surgical device.

According to an aspect of some embodiments of the present invention there is provided a method of piercing a tack into body tissue, the method comprising:

introducing a fastening device into the body adjacent to a tissue surface, the device including an inner tube and a fastener positioned in the inner tube;

rotating the inner tube, thereby linearly advancing the fastener in the inner tube and out of the inner tube into body tissue, without rotating the fastener in the body tissue.

According to some embodiments of the invention, rotating the inner tube further comprises advancing the fastener in the inner tube without rotating the fastener.

According to some embodiments of the invention, rotating the inner tube further comprises rotating the fastener within the inner tube at a different rate than the inner tube.

According to some embodiments of the invention, the fastener comprises a tack.

According to some embodiments of the invention, the fastening device further comprises at least one additional fastener having a threaded piercing portion and wherein the method further comprises:

rotating the inner tube thereby linearly advancing the additional fastener in the inner tube and out of the inner tube and rotating the threaded portion into body tissue.

According to an aspect of some embodiments of the present invention there is provided a method of piercing a tack into body tissue, the method comprising:

introducing a fastening device into the body adjacent a tissue surface, the device including an inner tube and at least two fasteners positioned in the inner tube;

rotating the inner tube, thereby linearly advancing the fasteners in the inner tube and out of the inner tube into tissue, wherein the two fasteners rotate at different rates during linear advancement.

According to some embodiments of the invention, rotating the inner tube further comprises rotating an advancing element positioned within the inner tube and comprising at least one threaded wing extending out of at least one slot of the inner tube, such that the threaded wing is threaded into inner threads of an outer tube in which the inner tube is positioned, thereby linearly advancing the advancing element within the inner tube.

According to some embodiments of the invention, advancing the fasteners comprises pushing the fasteners by the rotating advancing element.

According to some embodiments of the invention, the fastening device further comprises a shaft on which the fasteners are fitted and wherein rotating the inner tube comprises the inner tube without rotating the shaft.

According to some embodiments of the invention, the method further comprises:

moving the shaft without moving the fasteners.

According to some embodiments of the invention, the method further comprises:

pressing the device against body tissue, thereby exposing a needle end of the shaft.

According to some embodiments of the invention, the method further comprises:

threading a threaded end of the shaft into body tissue.

According to some embodiments of the invention, the method further comprises:

pushing at least two wires out of the fastening device and clamping the wires into body tissue.

According to an aspect of some embodiments of the present invention there is provided a fastening device comprising:

an inner tube comprising a proximal end and a distal end;

at least one fastener is positioned within the inner tube and adapted to advance linearly towards the distal end of the inner tube;

an advancing element which converts rotational motion to linear pushing force on the fastener.

According to some embodiments of the invention, the inner tube is adapted to rotate along its axis and provide the rotational motion to the advancing element.

According to some embodiments of the invention, the at least one fastener comprises two fasteners which are positioned within the inner tube and adapted to advance linearly towards the distal end of the inner tube, wherein the at least two fasteners are adapted to rotate at different rates during linear advancement.

According to some embodiments of the invention, at least one fastener of the at least one fastener has a geometry which does not rotate during linear advancement.

According to some embodiments of the invention, at least one fastener of the at least one fastener has a geometry which matches the geometry of the inner tube so that it rotates with the inner tube during linear advancement.

According to some embodiments of the invention, the same device is loaded with at least one rotating fastener and at least one non-rotating fastener at the same time.

According to some embodiments of the invention, the inner tube comprises at least one longitudinal slot along at least a portion of its length, the device comprising an internally threaded outer tube into which the inner tube is inserted, wherein the advancing element comprises at least one wing, the advancing element positioned within the inner tube such that the threads of the at least one wing protrude out of the at least one slot and are threaded in the inner threads of the outer tube; and wherein the at least one fastener is positioned within the inner tube between the advancing element and the distal end of the inner tube;

wherein rotation of the inner tube causes the threaded wing to advance along the inner threads of the outer tube and thereby to advance the advancing element and the fasteners linearly towards the distal end of the inner tube.

According to some embodiments of the invention, the outer tube does not move linearly with respect to the inner tube.

According to some embodiments of the invention, the inner tube is connected to a rotary drive mechanism of a surgical device.

According to some embodiments of the invention, the fasteners comprise a base and a piercing element and wherein at least one fastener comprises a cavity in its base for receiving a piercing element of another fastener.

According to some embodiments of the invention, at least two fasteners comprise interlocking elements adapted to connect the fasteners to each other such that the connected fasteners will rotate together.

According to some embodiments of the invention, the inner tube has a non-circular shaped cross-section and wherein at least one fastener comprises a non-circular shaped base having at least one common plane with the non-circular cross-section.

According to some embodiments of the invention, the device further comprises a shaft on which the fasteners are fitted and wherein the movement of the shaft is independent of the movement of the fasteners.

According to some embodiments of the invention, the shaft is smooth over at least 50% of its length.

According to some embodiments of the invention, the shaft comprises a sharpened distal end for piercing into body tissue.

According to some embodiments of the invention, the shaft is hollow and includes an inner shaft for protecting the sharpened end from harming body tissue, wherein the inner shaft is adapted to be pushed into the sharpened shaft when pushed against body tissue, thereby revealing the sharpened end.

According to some embodiments of the invention, the device comprises a distal end on which a spring is mounted, the spring surrounding the sharpened end of the shaft, such that when the spring is pressed against body tissue the sharpened end of the shaft is exposed.

According to some embodiments of the invention, the shaft is adapted to move in a linear direction only.

According to some embodiments of the invention, the device further comprises:
a shaft; and wherein, the at least one fastener comprises a bore along its length, wherein the bore is fitted onto the shaft,
wherein the fastener is adapted to move along the shaft.

According to some embodiments of the invention, the fastener is adapted to rotate around the shaft.

According to some embodiments of the invention, the shaft comprises a threaded end and the at least one fastener comprises a bore along its length, wherein the bore is fitted onto the shaft.

According to some embodiments of the invention, the shaft comprises a broadened distal end to prevent unintentional dislodgement of the fasteners from the shaft.

According to some embodiments of the invention, the device further comprises:
at least two wires having a relaxed state curved shape and forced straight into the device, the wires adapted to be pushed out of the distal end of the device and pierced into body tissue while returning to their relaxed curved shape, thereby clamping into the body tissue, wherein the wires are threaded through at least one of the bores in the fasteners and conduits in an outer tube of the device.

According to some embodiments of the invention, the wires are made of nickel titanium.

According to some embodiments of the invention, the fastening device is embodied in at least one of a straight distal section of a surgical device and a distal section of an articulating surgical device.

According to some embodiments of the invention, the inner tube has a longitudinal slot extending to the distal end of the inner tube and wherein at least one fastener comprises a base having at least one protrusion fitted into the slot.

According to some embodiments of the invention, the side walls of the protrusion extend outward in a 90 degree angle from the circumference of the fastener.

According to some embodiments of the invention, the inner tube has a circular shaped cross-section with a non-constant diameter and wherein at least one fastener comprises a circular shaped base having a non-constant diameter fitted to the inner tube.

According to some embodiments of the invention, the circular shaped cross-section with a non-constant diameter contains a flat or nearly flat side.

According to some embodiments of the invention, the inner tube has a cross-section with at least one indent and at least one fastener comprises a base having at least one protrusion fitted into the at least one indent of the inner tube.

According to some embodiments of the invention, the at least one protrusion is triangular shaped.

According to some embodiments of the invention, the at least one protrusion comprises a plurality of protrusions.

According to some embodiments of the invention, the inner tube contains a longitudinal slot which does not extend to the distal end of the inner tube and the at least one indent is provided as a groove which extends to the distal end.

According to some embodiments of the invention, the at least one fastener is threaded.

According to some embodiments of the invention, the pitch of the thread to the fastener provides linear movement when engaging tissue that is greater than provided by the linear pushing force.

According to some embodiments of the invention, the pitch of the thread to the fastener provides linear movement when engaging tissue that matches that provided by the linear pushing force.

According to some embodiments of the invention, the threads on two fasteners are arranged such that one fastener advances at a slower speed than a second fastener.

According to an aspect of some embodiments of the present invention there is provided a method of advancing a fastener, the method comprising:
introducing a fastening device outside a body, the device including an inner tube and a fastener positioned in the inner tube;
providing a rotational movement; and
converting the rotational movement into a linear pushing force on the fastener and linearly advancing the fastener in the inner tube.

According to some embodiments of the invention, rotating the inner tube further comprises advancing the fastener in the inner tube without rotating the fastener.

According to some embodiments of the invention, the fastening device further comprises at least one additional fastener having a threaded piercing portion and wherein the method further comprises:
rotating the inner tube thereby linearly advancing the additional fastener in the inner tube and out of the inner tube and rotating the threaded portion into body tissue.

According to some embodiments of the invention, at least one fastener of the at least one fastener does not rotate and at least one fastener rotates during linear advancement.

According to some embodiments of the invention, rotating the inner tube further comprises rotating an advancing element positioned within the inner tube and comprising at least one threaded wing extending out of at least one slot of the inner tube, such that the threaded wing is threaded into inner threads of an outer tube in which the inner tube is positioned, thereby linearly advancing the advancing element within the inner tube and advancing the fasteners by pushing thereon by the rotating advancing element.

According to some embodiments of the invention, the method further comprises:
pressing the device against body tissue, thereby exposing a needle end of a shaft.

According to some embodiments of the invention, the method further comprises:
threading a threaded end of a shaft into body tissue.

According to some embodiments of the invention, the method further comprises:
pushing at least two wires out of the fastening device and clamping the wires into body tissue.

According to some embodiments of the invention, the device is provided in contact with a body tissue and wherein the advancing comprises advancing the fastener into the body tissue.

According to an aspect of some embodiments of the present invention there is provided a method of advancing a threaded fastener into tissue, comprising:

pushing the fastener with a rotation speed and at a first speed different from a linear advancement speed provided by the fastener threads engaging tissue at the rotational speed.

According to an aspect of some embodiments of the present invention there is provided a method of piercing a tack into body tissue, the method comprising:

introducing a fastening device into the body adjacent a tissue surface, the device including an inner tube and a fastener positioned in the inner tube;

rotating the inner tube, thereby linearly advancing the fastener in the inner tube and out of the inner tube into body tissue, without rotating the fastener in the body tissue.

According to an aspect of some embodiments of the present invention there is provided a fastening device comprising:

a fastener advancer;
a first fastener; and
a second fastener, wherein the fastener advancer is configured to rotate the first fastener differently from the second fastener when advancing the fasteners into tissue at a same axial speed.

According to an aspect of some embodiments of the present invention there is provided a fastening device comprising:

a shaft adapted to penetrate body tissue; and
at least one tissue fastener having a bore along its length, wherein the bore is fitted onto the shaft and wherein the fastener is configured to travel along the shaft.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 10A-10E are schematic illustrations of attachment mechanisms in accordance with some other embodiments of the invention;

DESCRIPTION OF SPECIFIC EMBODIMENTS OF THE INVENTION

Figure 1A:
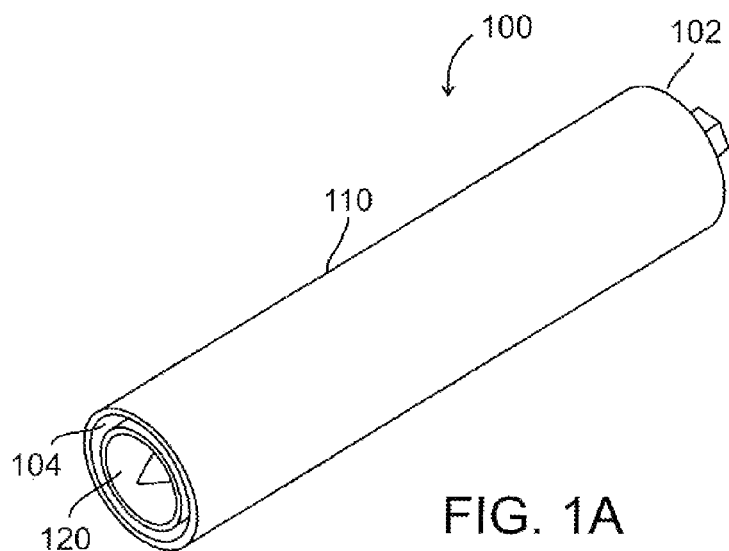
FIG. 1A is a schematic illustrations of a fastening device according to some embodiments of the invention.

The present invention, in some embodiments thereof, relates to a surgical instrument and, more particularly, but not exclusively, to a surgical fastening device.

A fastening device in accordance with some embodiments of the invention typically comprises an inner tube comprising a proximal end and a distal end and at least one fastener positioned within the inner tube and adapted to advance linearly towards the distal end of the inner tube, optionally by being pushed. Optionally, the fastener may rotate while and/or due to its advancing. In some exemplary embodiments of the invention, fasteners are inserted into body tissue directly or through networks, ribbons, mesh, straps, other fabrics and/or other objects, for example, to attach such objects to tissue and/or to attach two or more tissues together.

In some embodiments of the invention, the "fastening device" is provided as a straight device. In some alternative embodiments, the fastening device is at the end of an articulated handle, for example an endoscope or tool handles used for minimally invasive and/or keyhole surgery. Optionally, the fastener is advanced by a rotational motive force provided from a proximal side of the articulated handle.

An aspect of some embodiments of the present invention relates to a surgical fastening device, wherein the device converts rotational motion to a linear pushing force on the fastener. In an exemplary embodiment of the invention, the forward movement is not dependent on rotation of the fastener. Rather, in some embodiments, fastener rotation is caused by advancing motion and/or is provided directly or indirectly by the above rotational motion. In an exemplary embodiment of the invention, rotation of the fastener depends, at least in part, on fastener geometry, such that a fastener may be provided which is advanced but does not necessarily rotate while advancing. In some embodiments, at least one fastener is adapted to not rotate at all or to rotate at a rate not necessarily the same as any other fasteners or any other elements during linear advancement. In some embodiments, the same device is loaded with rotating and non-rotating fasteners at the same time. In an exemplary embodiment of the invention, the device includes an element, for example a non-rotating shaft on which said fastener rides and which has a non-circular cross section that locks to and prevents rotation of the fastener relative to the shaft.

In some embodiments, for example, using a fastener with threads, once fastener threads engage tissue the fastener threads cause the fastener on which they are threaded to advance at a speed different than the speed at which the device pushes the fastener.

A potential advantage of some embodiments of the invention is that even in an articulated system the fastening device can be used for one or more of pushing the fastener against tissue, compressing tissue and/or rotating the fastener into tissue. This pushing force applied via an articulated distal section of the device can be used to achieve desired tissue manipulation with reduced force and/or greater ease of application.

An aspect of some embodiments of the present invention relates to a surgical fastening device adapted to both push tacks and rotate threaded fasteners such as screws into the body.

In some embodiments of the invention, the term "fasteners" refers to elements adapted to pierce and/or embed into body tissue. Some fasteners may be used to attach medical devices or materials, such as a mesh, slings, hernia support materials, organ support materials, sutures, body tissue and others to body tissue, including soft tissues, ligaments and bones. For example, fasteners may include screws, tacks or a combination thereof. Fasteners may pass through networks, ribbons, mesh, straps, fabrics, and/or other objects and then engage into body tissue. It should be noted however, that the devices described herein may be used with a variety of fasteners, including fasteners not described herein.

In some exemplary embodiments of the invention, the fasteners comprise a base and a piercing element. Optionally, the piercing element may have a pointed tip for piercing into body tissue. In other embodiments, the piercing tip is hollow and initial tissue penetration is provided by an insert, such as a shaft. In other embodiments, the piecing element is replaced by a blunt tip or other non-penetrating tip, for example, for insertion into a pre-existing hole in tissue.

In an exemplary embodiment of the invention, the piercing element is narrower than the base and/or has a tapering shape. Fasteners may be permanently or removably attached to body tissue. For example, a fastener may include a socket in the base for reverse rotation and unscrewing or for engaging and retraction thereof. Optionally, the fasteners are biodegradable.

In some embodiments, the fasteners may change their shape when within body tissue, for example, the fasteners may squeeze or expand when within body tissue to secure the fasteners into the tissue. Optionally the fasteners are hollow, for example, enabling tissue to grow through them. Optionally or alternatively, a fastener is covered and/or elutes one or more bioactive materials and/or includes one or more sections with tissue adhesive or ingrowth encouraging sections. Optionally or alternatively, the fastener includes one or more areas adapted to prevent tissue adhesion thereto In some embodiments of the invention, screw-type fasteners are provided which are fastened in body tissue by rotation. In some embodiments, the screws comprise a threaded portion on the outer surface of the piercing element. In some embodiments, the screws are helical coils or spring-like elements.

In some embodiments of the invention, tack-like fasteners or wedging devices are provided, which are fastened to body tissue by linear force. In some embodiments, the tacks do not have a threaded portion on the outer surface of the body. In some embodiments, the tacks can also rotate within the tissue and/or includes a threading. In other embodiments, the tacks are adapted to be pushed into body tissue and should not rotate in the tissue, for example such tacks may include an anti-rotation feature which interferes with the rotational geometry of the piercing element. In one example, a tack comprises a base and at least two separated piercing elements substantially perpendicular to the base.

In some embodiments of the invention, the surgical fastening device comprises an inner tube housing a plurality of fasteners. The inner tube optionally comprises a distal end positioned at or near body tissue into which fasteners are to be deployed and a proximal end close to the practitioner's hand holding the surgical fastening device. When the fastening device is used inside the body, the distal end would normally be inside the body and the proximal side, or part of it, may be outside the body.

In some embodiments, at least one longitudinal (or spiral) slot is provided over a portion of the inner tube's length. Optionally, two, three, four or more optionally parallel slots are provided. Optionally, the slot extends to a distal end of the inner tube. In some embodiments, the at least one longitudinal slot does not extend to the distal end of the inner tube and/or does not extend to the proximal end of the inner tube. Optionally, the unslotted portions form a bridge at one or both of the distal and proximal ends of the inner tube. In some embodiments, the bridges provide increased strength, rigidity and/or stability, which may be advantageous for the fastening of certain objects and/or for mechanical operation of the device.

In an exemplary embodiment of the invention, an advancing element is provided, designed to fit into the inner tube, optionally having at least one threaded wing that fits from the inside outwards into the at least one slot of the inner tube, such that the threads of the threaded wing extend out of the slot. The wing is preferably substantially shorter than the slot's length and is able to slide along the slot. The number of wings of the advancing element optionally corresponds to the number and circumferential positioning of slots of the inner tube, i.e. if the inner tube has two slots, the advancing elements has two corresponding wings, etc., although the advancing element may have fewer wings than the number of slots.

In an exemplary embodiment of the invention, the inner tube fits into an internally threaded outer tube, such that the threads of the advancing element that extend out of the slot of the inner tube are threaded into the internal threads of the outer tube. When the inner tube is rotated with respect to the outer tube, the advancing element advances along the threads of the outer tube without rotating the outer tube with respect to the inner tube. The outer tube is preferably static and does not move with respect to other elements of fastening device. Alternatively, the movement of the outer tube is independent of the movement of the inner tube and advancing element.

In an exemplary embodiment of the invention, at least one fastener is positioned between the advancing element and the distal end of the inner tube. During (for example) clock-wise rotation of the inner tube with respect to the outer tube, the threads of the advancing element rotate within the internal thread of the outer tube, thereby linearly advancing the advancing element towards the distal end of the tube. The fasteners located between the advancing element and the distal end are urged forward by the advancing element, as it turns in clock-wise direction, towards the distal end of the inner tube and out of the tube.

In some embodiments, the inner tube may also rotate (for example) counter-clock wise thereby causing the advancing element to retract linearly towards the proximal end of the device. Clock-wise and counter-clock wise rotation may be performed successively in order to cause micro hammer like movements or vibrations.

When the slot spirals, this may cause the linear pushing force to include a rotational component. Optionally, the advancing element does not rotationally engage the fasteners. In other embodiments, the advancing element rotationally engages the fasteners and/or a shaft, if any.

The term "rotation" as used to describe some embodiments of the invention, refers to a rotary motion around a longitudinal axis of the object that rotates, unless otherwise defined. For example, the inner tube rotates means the inner tube rotates around its longitudinal axis. Clock-wise rotation and counter clock-wise rotation are used as example only and can be interchanged in accordance with the direction of the threads in embodiments of the invention.

The term "linear movement" as used to describe some embodiments of the invention refers to movement along a longitudinal axis of the object that moves, unless otherwise defined. For example, linear movement of the fasteners comprises movement along the longitudinal axis of the fasteners. "Linear advancement" or "advancement" refers to linear movement towards the distal end of the inner tube or device and the term "linear retraction" or "retraction" refers to linear movement towards the proximal end of the inner tube or device.

In some embodiments of the invention, the piercing element (or tip) of a fastener fits into a cavity in the base of another fastener. The depth of the cavity can be chosen so as to increase the number and/or length of fasteners (e.g., 1, 2, 4, 6, 8 or intermediate or greater numbers) that can be inserted in the inner tube at a given length. Optionally, the advancing element has a protrusion or protrusions that fit into a cavity in the base of a fastener, thereby centering the fasteners in the inner tube.

An aspect of some embodiments of the present invention relates to a surgical fastening device adapted to push tacks into body tissue without rotating the tacks themselves, by applying rotational force to the fastening device.

An aspect of some embodiments of the invention, relates to a surgical fastening device wherein at least two fasteners positioned in the device rotate at different rates and/or direction during linear advancement. Optionally, some of the fasteners located within the tube may be pushed out of the inner tube without rotation while other fasteners located in the inner tube may rotate during linear advancement out of the tube. Optionally, the at least two fasteners are adapted to rotate at a different rate than any other fasteners and any other elements during linear advancement, or to not rotate at all. In these embodiments, the inner tube may include both screws and tacks together and apply both to the tissue using appropriate motion for each.

In some embodiments, the fasteners comprise interlocking elements adapted to connect the fasteners to each other, optionally providing co-rotation.

The tip (or piercing element) of a fastener may include depressions, and the cavity of a fastener may include protrusions formed to fit into and optionally interlock with the depressions. Thus, by connecting a piercing element with depressions to a cavity with interlocking protrusions, for example, the two connected fasteners will either rotate or not rotate together, at the same rate and direction. However, if a smooth piercing element is connected to a cavity having depressions or protrusions (or a smooth cavity to a piercing element having depressions or protrusions), the rotation of one of the fasteners will not be dependent on the rotation of the other fastener.

According to some embodiments, the advancing element is provided with a tip having depressions. Since the advancing element rotates, any fasteners having interlocking protrusions in their cavities connected in a row will rotate along with the advancing element. Fasteners having smooth or depressed cavities, or no cavities, stacked thereon will not rotate in conjunction with the advancing element.

In these embodiments, the surgical fastening device optionally includes (e.g., loaded at a factory or in a hospital or surgery) tacks and screws in a desired order, meaning that the fastening device will first apply tacks and then screws, unless other means causing rotation of the fasteners are provided.

In some embodiments, the inner tube has a circular shaped inner cross section. In some embodiments, the fasteners have a circular shaped base, which may, for example, allow them to not rotate with the inner tube.

In an exemplary embodiment of the invention, the inner tube geometry and fastener geometry are matched so that the fastener rotates with the tube and/or its rotation is otherwise affected by the tube.

In some embodiments of the invention, the inner tube comprises a non-circular shaped inner cross section, for example a polygonal such as a hexagonal, pentagonal, square, triangular or other non-circular shaped cross section or a circular shaped cross section of the inner tube with a non-constant diameter or one or more indents to accommodate protrusions emanating from the base of the fasteners. Optionally, some fasteners comprise a base shaped to fit the inner non-circular cross-section of the inner tube, such that they will rotate with the inner tube. Optionally, some fasteners comprise a base shaped to fit the inner non-circular cross-section of the inner tube, such that they will not rotate with the advancing element. Alternatively, some fasteners comprise a base having at least one protrusion fitted into at least one groove formed along the inside of the inner tube. A potential advantage of a groove over a slot as described below is that the groove, not being through, weakens the inner tube to a lesser extent.

In some embodiments, the circular shaped cross section with a non-constant diameter and the corresponding fastener with a non-constant diameter fitted to it, comprise at least one flat or nearly flat side. Alternatively, some fasteners comprise one or more wings. Optionally, the wings of the fasteners fit into one or more slots of the inner tube which are used for the advancing element.

In some embodiments, the inner tube has a slot extending to the distal end of the inner tube and at least one fastener comprises a base having at least one wing (protrusion) fitted into said slot. In a generally rectangular wing, the wing has two side walls and an end wall or tip. Optionally, the side walls of the wing, are perpendicular to the circumference of the fastener, extending outward in a 90 degree angle from the circumference of the fastener, and fit inside said slot and make contact with the surface of the inner tube which reaches to the slot, interfering with the rotation of the fastener. Optionally or alternatively, the side walls are about perpendicular to the walls of the slot. Alternatively, the side walls of the wing extend out from the circumference of the fastener at an angle less than 90 degrees between the side wall and the part of the circumference of the fastener which is outside of the wing, so that the front and back walls of the wing are broader distally than proximally to the fastener. A potential advantage of these geometries is that the side walls do not push the inner tube when making contact with the inner tube and relative rotation is provided.

Optionally, the number of protrusions is one or two. Optionally there are more than two protrusions. Optionally, the at least one protrusion is triangular or nearly triangular in shape. Optionally, the number of triangular or nearly triangular protrusions is four. Optionally there are more or less than four triangular or nearly triangular protrusions.

In some embodiments, a fastener includes a plurality of protrusions thereon. Optionally, the protrusions are of the same size. Alternatively, the protrusions are not of the same size. Optionally, the protrusions are equidistant from each other around the circumference. Alternatively, the protrusions are not equidistant from each other. Optionally, the protrusions are positioned so as to be symmetrical between one half of the circumference of the fastener and the other half. Alternatively, the protrusions are positioned so as not to be symmetrical. The different positions of the protrusions may provide different levels of strength, rigidity and/or stability. The differences in the shapes of the protrusions lead to different alignments of the fasteners once the protrusions are matched with corresponding slots in the inner tube. The alignment may be used to dictate the relative orientation of the fastening device and the position of the beginning of the thread located on the fastener. The desired threading position and level of strength, rigidity and/or stability of the fastener may depend on the particular object being fastened, so that different positions of protrusions may be advantageous for the fastening of different objects.

In some embodiments, the inner tube contains a longitudinal slot which does not extend to the distal end of said inner tube and the at least one indent is positioned on the bridge of the inner tube located at the end of said slot. Optionally, the bridge increases the stability and/or rigidity of the fastening device.

Optionally, some other fasteners may comprise a base having a different shape than the inner cross section of the inner tube, such that they will not rotate at the same rate and/or direction as the inner tube, but will essentially move linearly due to force provided by the advancing fasteners and/or by the advancing element. Optionally, the different shape base fasteners will not rotate at all during linear advancement or during advancement out of the inner tube. The surgical fastening device may thus linearly push tacks into body tissue without rotating the tacks as they penetrate the tissue, by applying rotary force to the inner tube.

In these embodiments, the inner tube may comprise both matching base fasteners and non-matching base fasteners and the matching base fasteners will rotate along with the inner tube during linear displacement while the non-matching base fasteners may not rotate or rotate at different rate and/or direction than the inner tube during linear displacement. Optionally, at least one matching based fastener is a screw. Optionally, at least one non-matching fastener is a tack.

In these embodiments, the surgical fastening device can provide a mixture of screws and tacks in the inner tube and they do not need to be loaded in any particular order. The fasteners can be provided with or without cavities in their base.

In some embodiments of the present invention, the fasteners are positioned in the inner tube with no element provided passing through the fasteners.

An aspect of some embodiments of the present invention relates to a surgical fastening device comprising a shaft on which fasteners are positioned, where the movement of the shaft, if any may be independent of the movement of the fasteners. Optionally, the shaft rotates with the fasteners. Alternatively, the fastener rotates independently of the fasteners. Optionally, the shaft lies in a bore formed in the fasteners. In an alternative embodiment, the shaft lies in a slot formed in the side of the fasteners.

In some embodiments, at least one fastener and/or the advancing element has an internal hollow space, creating a bore along its length. Optionally, the shaft is fitted to go through the bore of the fastener and/or the advancing element.

In some embodiments of the invention, the outer surface of the shaft is smooth. Optionally, the outer surface of the shaft is smooth along at least 50%, 60%, 80% or 90% of the length of the shaft.

In some embodiments, the shaft comprises a needle having a sharpened distal end or tip for piercing into body tissue. In some embodiments, the shaft does not have a sharpened end, but may be used for tissue penetration and/or stabilization in a pierced tissue.

Optionally, the fasteners comprise no sharpened end and the needle assists in piercing the fasteners into body tissue.

A potential advantage of using a shaft for tissue penetration rather than or in addition to a tip of a fastener is that the sharpened distal end of the shaft pierces the skin and the mechanical requirements of the fasteners are possibly reduced. Another potential advantage is that the fasteners, which remain in the body tissue after the insertion of the implants, do not have sharp points, while the shaft, with its sharpened end, is removed from the body tissue after the insertion of the fasteners and implants, reducing the change of later internal damage caused by the fasteners. In some embodiments, the shaft can be retracted when not needed.

In some embodiments, the shaft is static and does not move relative to the inner and outer tube. Optionally, the shaft can move linearly along the length of the inner tube in order to pierce into body tissue. Optionally, the shaft rotates about its axis. The movement of the shaft may be independent of the movement of the fasteners, i.e. the fasteners may move while the shaft is static and the shaft may move while the fasteners are static, or both may move at different directions and/or rates. In some embodiments, the shaft has a geometry which allows the fastener to rotationally lock to it and/or has a geometry, such as spiral protrusions, which allows or causes the fasteners to rotate relative to it as they advance.

In some embodiments of the invention, the surgical fastening device comprises means for preventing unintentional dislodging of the fasteners from the inner tube. Optionally, a protrusion or a lip is provided near the proximal end at the inner side of the inner tube, adapted to hold the distal-most fastener and prevent its unintentional dislodging. In some embodiments of the invention, where a shaft is provided, the shaft comprises a distal end located at the distal end of the device and a proximal end located at the proximal end of the device. Optionally, the distal end of the shaft is broader than the proximal end thereof, requiring that some force be exerted on a fastener in order for the fastener to pass over the broader shaft end. Optionally, when the shaft is a needle having a sharpened edge at its distal end, the distal broadened edge of the shaft is provided proximal to the distal sharpened edge.

An aspect of some embodiments of the present invention relates to a surgical fastening device comprising an attachment mechanism for temporarily attaching body tissue to the distal end of the fastening device. The attachment mechanism can reduce the linear force required to be applied by the fastening device and/or may align the fastening device with the tissue so that the fasteners will pierce tissue wall while the device is flush with tissue surface and/or being substantially perpendicular thereto.

In some embodiments of the invention, the at least one fastener is threaded. In some embodiments, the pitch of the thread to the fastener is constant. In some embodiments, the pitch of the thread is variable between fasteners and/or in a single fastener.

In some embodiments, once fastener threads engage tissue, the fastener threads cause the fastener to which they belong to advance at a speed different than the speed at which the device pushes the fastener. For example, the pitch of the thread to the fastener may be greater than the pitch of the shaft. This may be useful when implanting objects for which it is beneficial to advance the objects more quickly than the progression of the advancing element once the object enters the body. This may also be used for compressing and/or collecting the tissue.

In another example, the pitch of the thread to the fastener may be equal to the pitch of the shaft. This may be useful when implanting objects for which it is beneficial to advance the objects at a rate equal to the progression of the advancing element once the object enters the body.

In another example, the pitch of the thread to the fastener may be less than the pitch of the shaft. This may be useful when implanting objects for which it is beneficial to advance the objects more slowly than the progression of the advancing element once the object enters the body. A potential advantage is that using a fastener which advances at a slower speed than a second fastener which enters the body tissue after the first fastener may cause a compression of the body tissue and a more secure fastening.

In some embodiments of the invention, where a needle is provided, the attachment mechanism may be in the form of a thread provided on the sharpened edge of the needle. The needle is rotated so that the needle point is threaded into body tissue and the tissue is essentially drawn closer towards the distal end of the device while the device aligns with the tissue. The fasteners can then more easily pierce and/or be threaded into the body tissue.

In some embodiments, the attachment mechanism is provided in the form of thin wires having a relaxed curved shape and forced straight in the fastening device. The wires move linearly with respect to the device out of the distal end of the device and into body tissue. When advanced out of the device, the distal ends of the wires return to their relaxed curved shape and are firmly clamped into the body tissue, thereby drawing the tissue closer to the distal end of the fastening device and/or aligning the fastening device with the tissue.

In some embodiments, the wires are threaded through conduits in the outer tube. In some embodiments, the wires are provided through bores in the fasteners/and or the shaft where provided.

In some embodiments, two wires are provided. Alternatively, any other number of wires can be provided, for example between 3-10 wires.

Optionally, the wires are made of nickel titanium alloy.

In some embodiments of the invention, the fastening device is used outside the body, for example, prior to surgery, for example, to advance a fastener prior to use of the fastening device with body tissue.

Before explaining at least one embodiment of the invention in detail, it is to be understood that the invention is not necessarily limited in its application to the details of construction and the arrangement of the components and/or methods set forth in the following description and/or illustrated in the drawings. The invention is capable of other embodiments or of being practiced or carried out in various ways.

Referring now to the drawings, FIG. 1A illustrates a fastening device 100 in accordance with some embodiments of the invention. Device 100 has a proximal end 102 at the side close to the practitioner's hand and a distal end 104 at the side adapted to contact body tissue. These proximal and distal denotations will be used throughout the document to describe the ends of various different elements of the device.

Figure 1B:
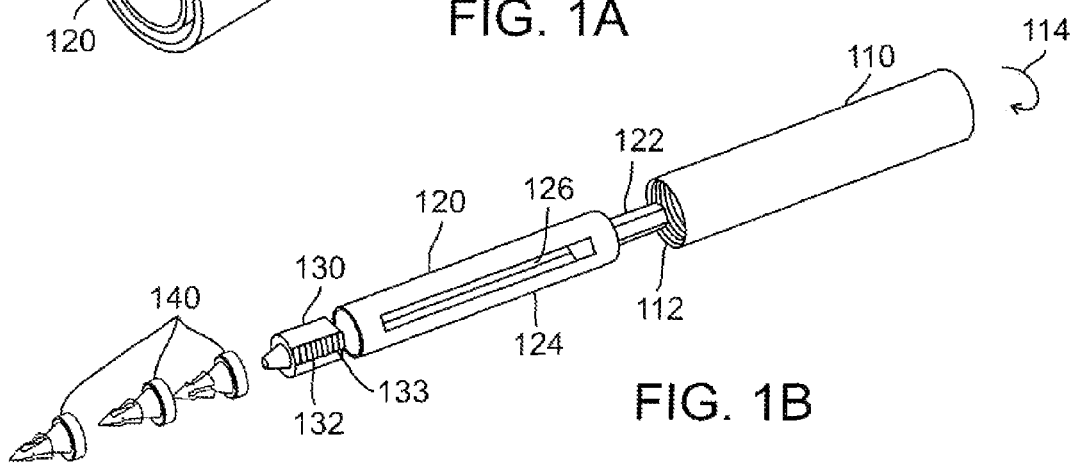
FIG. 1B is an exploded view of elements of the fastening device of FIG. 1A according to some embodiments of the invention.

FIG. 1B is an exploded view of the elements of device 100. Device 100 includes an outer tube 110 which preferably comprises threads 112 in its inner surface. Outer tube 110 preferably fits into regular trocars, such as a 5.5 mm trocar. Optionally, the diameter of the outer tube is between 2.5-7.5 mm, for example between 4-6 mm.

An inner tube 120 is fitted into outer tube 110. Inner tube 120 optionally comprises a proximal portion 122 for transferring rotary force to the inner tube and a distal portion 124 for receiving fasteners therein. Optionally, the proximal portion is narrower than the distal portion. Distal portion 124 comprises at least one longitudinal slot 126 along at least a portion of its length. Two, three, four or more slots may be provided in accordance with exemplary embodiments of the invention.

An advancing element 130 comprises at least one threaded wing 132 and fits into inner tube 120, such that threads 133 on wing 132 extend out of slot 126 and are threaded into inner threads 112 of outer tube 110. Wing 132 is preferably substantially shorter than the length of slot 126 and is able to slide along the slot. The number of wings of advancing element 130 optionally corresponds to the number and circumferential positioning of slots of inner tube 120, although advancing element 130 may have fewer wings than the number of slots 126 of inner tube 120.

In some embodiments, the width of the wings is substantially the same as the width of the slot. Alternatively, the portion of the wing that extends out of the slot is wider than the width of the slot. Optionally, the portion of the wing that extends out of the slot surrounds part or all of the circumference of the inner tube, as shown in FIG. 1F for example. In this case, the wings of advancing element 130 may have interconnected thread 133.

Advancing element 130 optionally has an external diameter of 0.5-1 mm less than the diameter of the outer tube, for example a diameter of between 3-5.5 mm. The length of the advancing element is optionally at least 1.25×D.

Outer tube 110, inner tube 120 and advancing element 130 are optionally made of biocompatible metals or polymers, such as stainless steel 316, SS 17-4 or PEEK.

During rotation of inner tube 120, advancing element 130 is threaded in the threads of outer tube 110. Clock-wise rotation in the direction 114 causes movement of the advancing element along the inner threads of the outer tube and thereby linear advancement towards the distal end of inner tube 120. Counter clock-wise rotation causes linear retraction of the advancing element towards the proximal end of the tube. Clock-wise and counter clock-wise rotation are used as examples only and could be interchanged according to the direction of the threads in the outer tube and on the advancing element in embodiments of the invention.

Outer tube 110 is preferably static and does not move with respect to the inner tube or other elements of the fastening device. In some embodiments, at least a portion of outer tube 110 may move linearly.

At least one fastener 140 is provided distal to the advancing element. Optionally, between 1 and 15 fasteners are provided in the inner tube. In an exemplary embodiment of the invention, a fastener length is between 1 and 30 mm, for example, between 2 and 15 mm. In an exemplary embodiment of the invention, the diameter of a fastener is between 1 and 30 mm, for example, between 2 and 15 mm. In an exemplary embodiment of the invention, the fasteners are medical grade sterilized objects made of biocompatible materials and suitable for surgical implantation and optionally remaining in the body for over a week, a month and/or a year.

For the threads shown, by clock-wise rotation of inner tube 120 and linear advancement of advancing element 130, the advancing element pushes the fasteners towards the distal end of the inner tube, and out of the tube. In some embodiments, the device converts rotational motion to linear pushing force on the fastener which movement is not caused by the rotation of the fastener, which rotation of the fastener may depend on the fastener geometry. In some embodiments, at least one fastener is adapted to not rotate at all or to rotate at a rate not necessarily the same as any other fasteners or any other elements during linear advancement. In some embodiments, the same device is loaded with rotating and non-rotating fasteners at the same time.

During counter-clock-wise rotation of the inner tube and linear retraction of advancing element, the fasteners may either linearly retract with the advancing element or remain static. Successive clock-wise and counter-clock wise rotation may cause micro-hammer-like movements of the fastener and assist in penetrating the fasteners into the tissue. The movements may be caused either by successive retraction and advancement of the fastener or by the advancing element hitting the fastener during each linear advancement.

In some embodiments of the invention, fasteners may rotate during linear advancement in conjunction with the inner tube. In some embodiments, rotation of the inner tube causes linear advancement of the fasteners without rotating the fasteners or by rotating the fasteners at a different rate and/or direction than the inner tube. In some embodiments, some fasteners located in the inner tube may rotate in conjunction with the inner tube while other fasteners located in the inner tube may not rotate or may rotate at different rates and/or directions than the inner tube as will be described with respect to FIGS. 3 and 4 below. Optionally, at least two fasteners positioned in the inner tube rotate at different rates and/or directions.

Figure 1C:
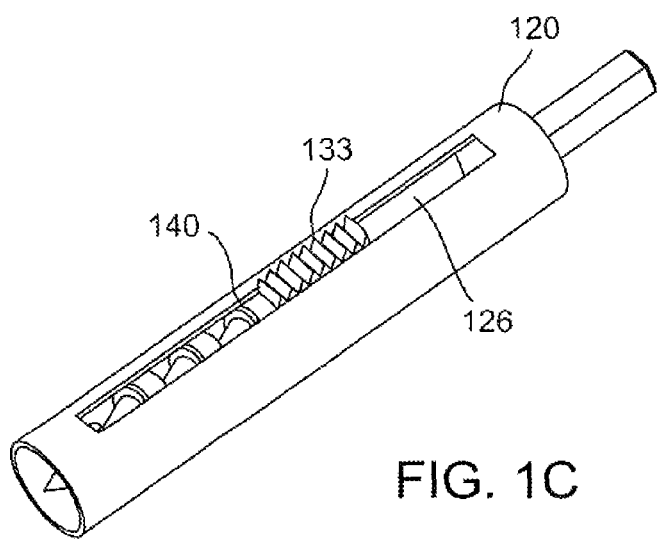
FIG. 1C is a schematic illustration of an inner tube with an advancing element and fastener used in the device of FIG. 1A according to some embodiments of the invention.

FIG. 1C is a schematic illustration of inner tube 120 including advancing element 130 and fasteners 140.

Figure 1D:
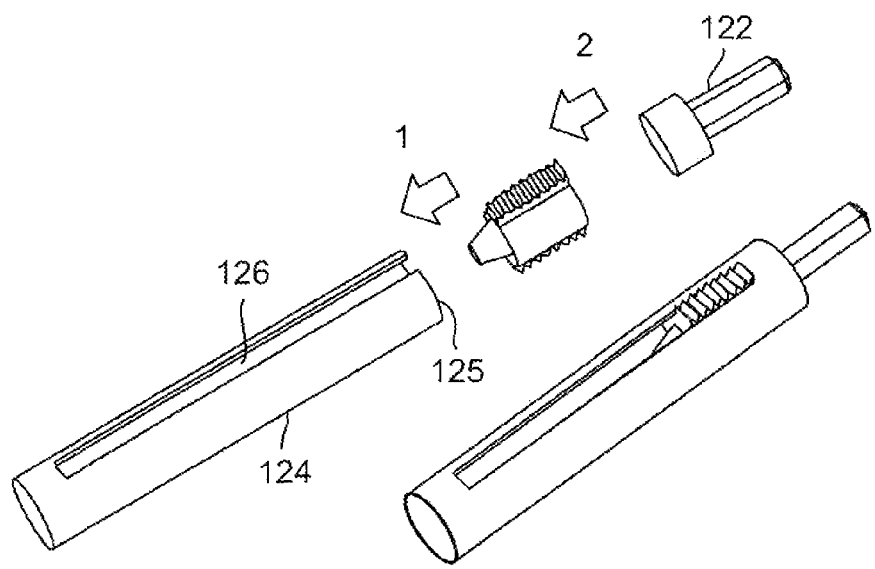
FIGS. 1D and 1E are schematic illustrations of methods of inserting an advancing element and fasteners in the inner tube of FIG. 1C according to some embodiments of the invention.
Figure 1E:
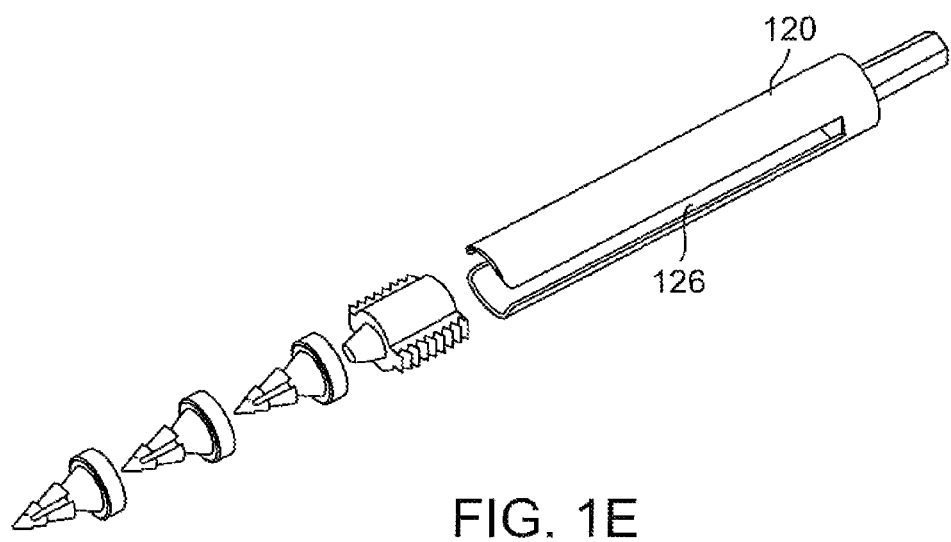
Figure 1F:
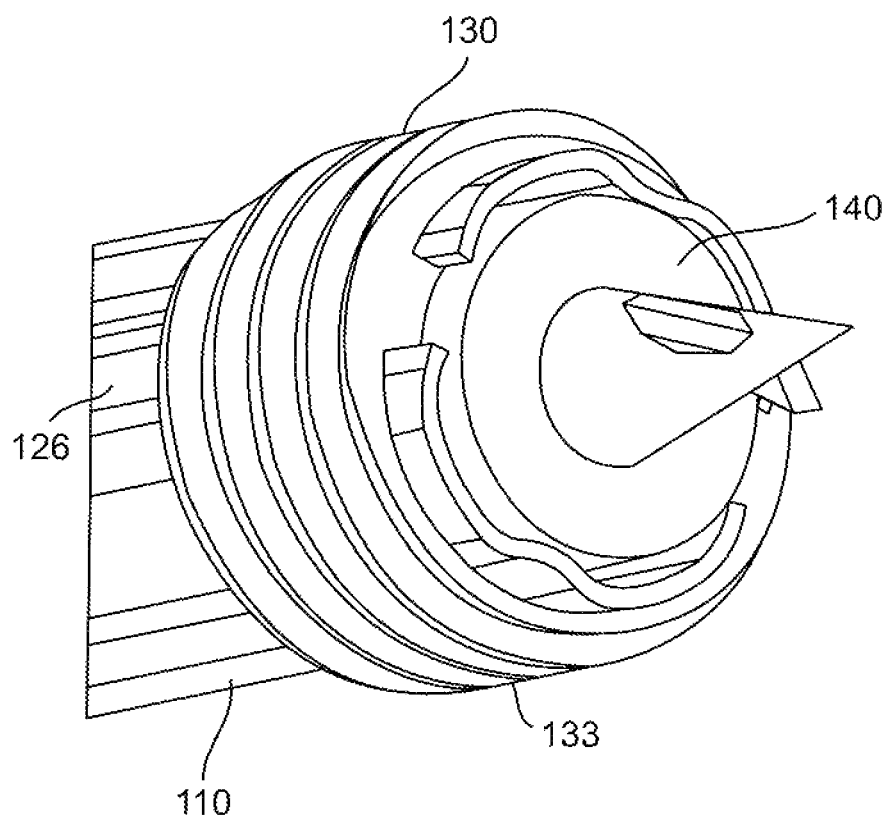
FIG. 1F is a schematic illustration of an inner tube with an advancing element and fastener used in the device of FIG. 1A according to some other embodiments of the invention.

FIGS. 1D and 1E are schematic illustrations showing how the advancing element and/or fasteners are fitted into the inner tube. FIG. 1D illustrates an embodiment where inner tube 120 is separable into a proximal portion 122 and a distal portion 124, where the at least one slot 126 extends till the proximal end 125 of distal portion 124. In some embodiments of the invention Advancing element 130 and/or fasteners are loaded into inner tube 120 from either the proximal or distal side.

FIG. 1E illustrates a different embodiment where slot 126 extends till the distal end of inner tube 120. In this embodiment, advancing element and fasteners can both be inserted to the inner tube via the distal end of the slot. In this embodiment, care should be taken so that advancing element will not eject out of the inner tube when in the body of a patient. For example, the number of rotations of the inner tube may be limited by a mechanism located in the handle operating the device.

In most of the illustrated embodiments, the method of FIG. 1D is used to load the device. For simplicity, the details of closure of the proximal end are not shown.

Any type of fasteners may be used according to embodiments of the invention. The fasteners may be made of any material, for example biocompatible absorbable and non-absorbable materials, and may have any diameter that will fit into the inner tube, for example having a diameter of between 2-5.5 mm. The fasteners may include screws adapted to be threaded into body tissue and/or tacks adapted to be pushed into body tissue. The tacks may either be tacks that can rotate in the body or tacks adapted to be forced linearly in the tissue without rotation. In some embodiments, the inner tube may include together fasteners of different types, shapes, materials and/or diameters. Some specific characteristic of fasteners may provide advantages/disadvantages to the device and the way of its operation, as will be described below.

Figure 2A:
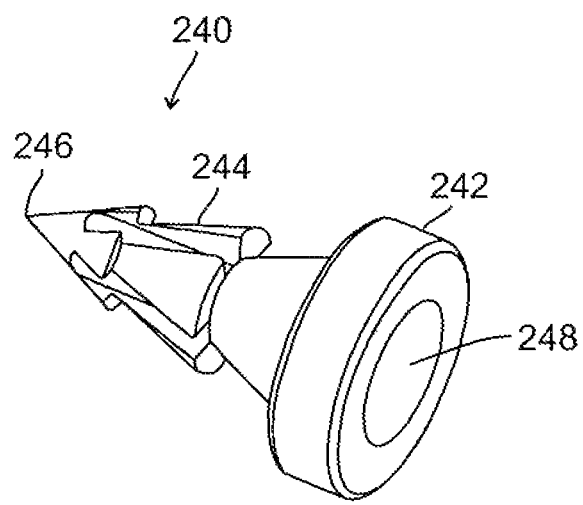
FIGS. 2A-2D are schematic illustrations of fasteners to be used with the device of FIG. 1 according to some embodiments of the invention.

FIG. 2A is a schematic illustration of a fastener 240 in accordance with an exemplary embodiment of the invention which may be used with fastening device 100. Fastener 240 includes a base 242 and an optionally narrower piercing element 244, optionally having a tip 246. Tip 246 may be sharpened and adapted to be pierced into body tissue. Fastener 240 is shown in FIG. 2A as a tack, however, screws may also be used according to embodiments of the present invention.

Figure 2B:
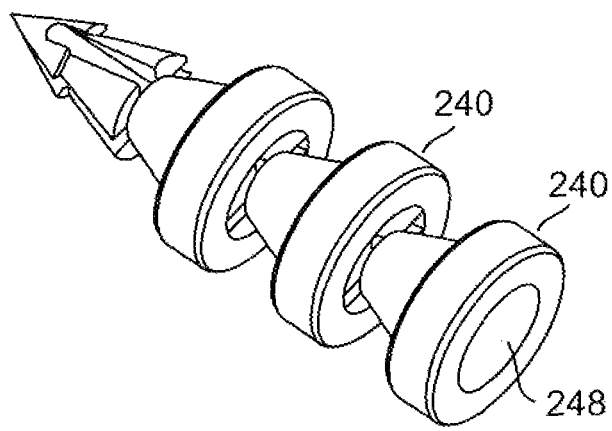
Figures 2C, 2D:
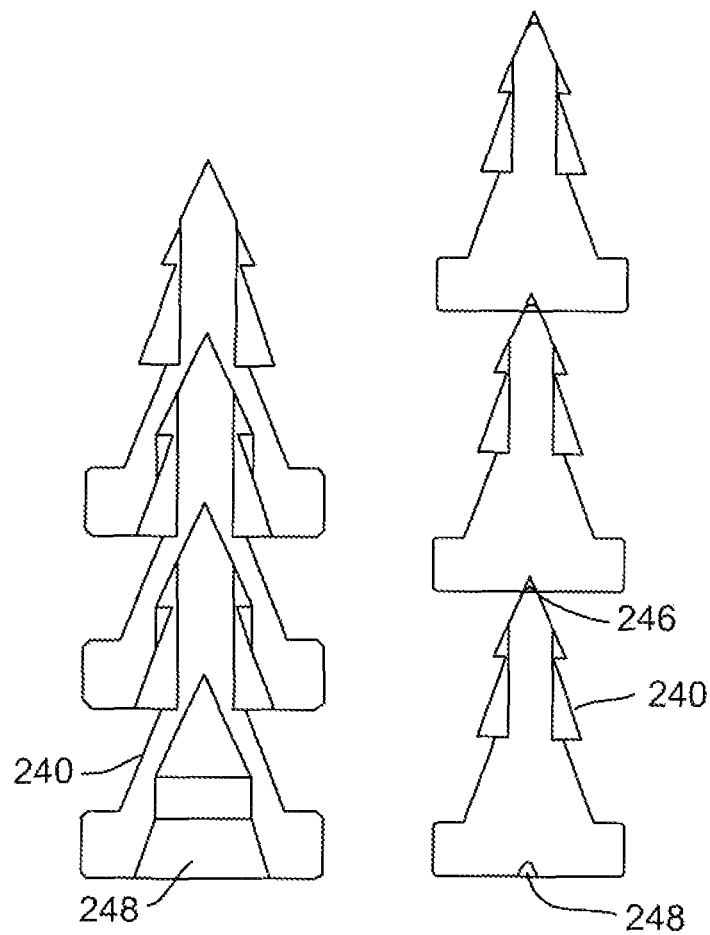

In some embodiments, a cavity 248 is provided in base 242 adapted to receive the tip or piercing element of another fastener thereby enabling stacking of fasteners as shown in FIG. 2B. The dimensions of cavity 248 may be chosen in accordance with the number of fasteners desired to be inserted into the inner tube. FIG. 2C shows an example of stacked fasteners having relatively shallow cavities 248 and FIG. 2D shows an example of stacked fasteners having relatively deep cavities 248. It can be seen from the figures that the deeper the cavities, the more fasteners can be stacked in a given length.

Figure 2E:
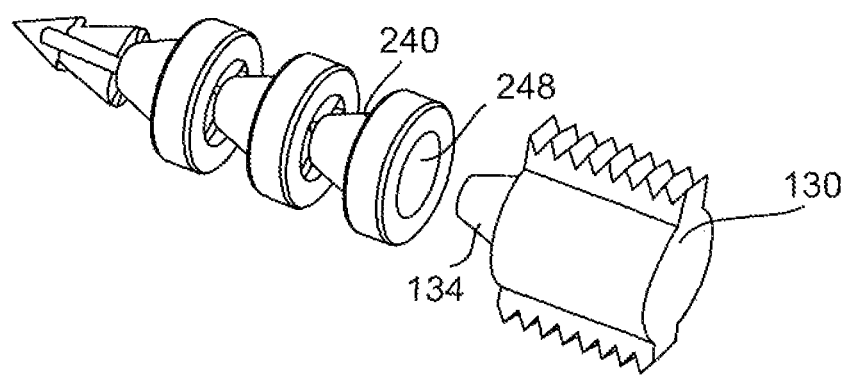
FIG. 2E is a schematic illustration of an advancing element in conjunction with a stack of fasteners to be used with the fasteners shown in FIGS. 2A-2D in the device of FIG. 1 according to some embodiments of the invention.
Figure 2F:
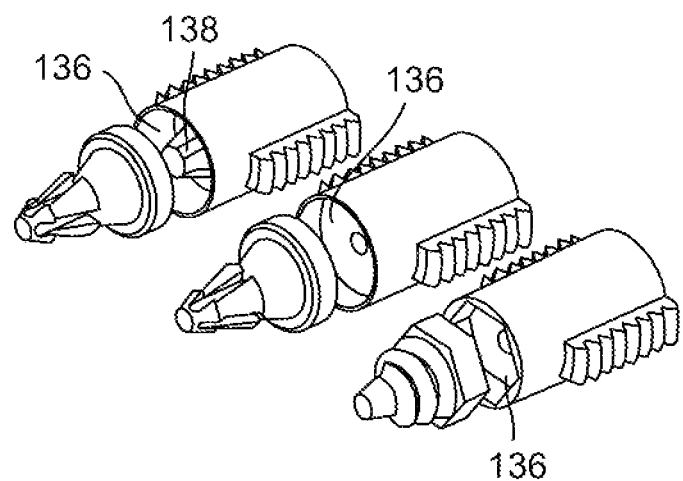
FIG. 2F is a schematic illustration of an advancing element in conjunction with a fasteners to be used in the device of FIG. 1 according to some other embodiments of the invention.

In some embodiments of the invention, advancing element 130 has a tip 134 optionally adapted to be inserted into a cavity 248 of a fastener 240 as shown in FIG. 2E. Protrusion 134 centers the fasteners in the inner tube. Optionally, the advancing element comprises other means of centering the fasteners in the inner tube, as shown in FIG. 2F for example. The advancing elements may include a recess 136 in the form of the base of an advancing element. Optionally, a protrusion 138 is provided in the recess.

FIGS. 3 and 4 illustrate exemplary embodiments where two fasteners located in the same inner tube rotate at different rates and/or directions. Optionally, some fasteners located within the inner tube rotate along with the inner tube during linear displacement while other fasteners located within the inner tube move linearly without rotating or rotate at a different rate and/or direction than the inner tube. Optionally, at least one fastener located in the inner tube rotates during linear displacement within the inner tube and does not rotate when being pushed out of the tube. In these embodiments, the inner tube may include both screws and tacks together and apply both to the tissue using appropriate motion for each.

The embodiments shown in FIGS. 3 and 4 may be useful for example for introducing both screws and tacks into body tissue using the same fastening device without having to withdraw the fastening device or parts thereof out of the body for reloading during the procedure. The fastening device of the present invention can rotate the screws and push the tacks into body tissue in a continuous procedure.

FIGS. 3 and 4 show specific type of fasteners for illustration only. The fasteners according to embodiments of the invention may comprises, tacks, screws or a mix thereof. In addition, fasteners according to embodiments of the invention may have different shapes and diameters and include the elements described hereinafter causing rotation or non-rotation thereof. The embodiments shown in FIGS. 3 and 4 may be used with fastening device 100 shown in FIG. 1 with the necessary changes described hereinafter.

Figure 3A:
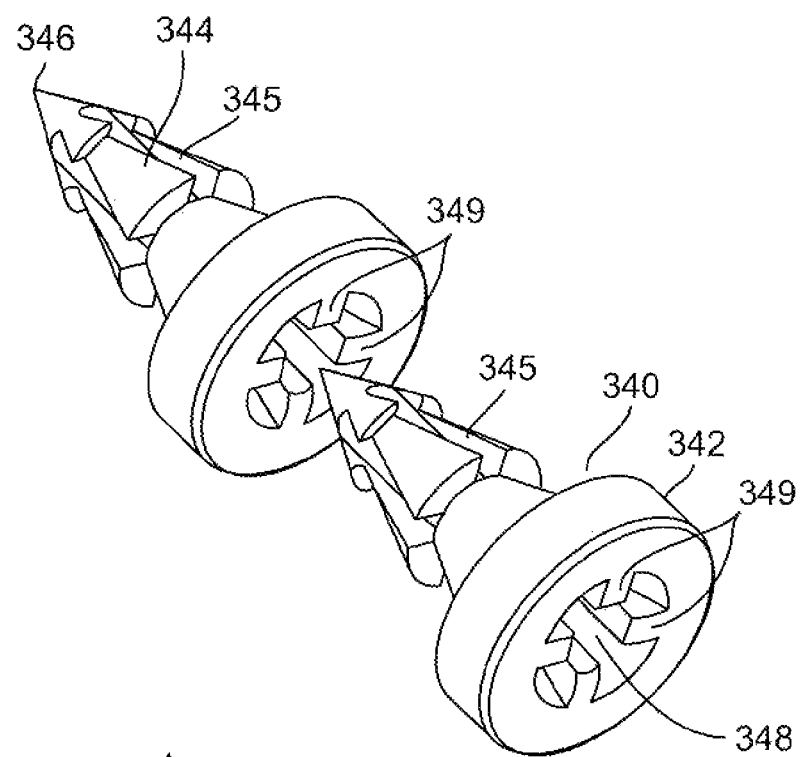
FIGS. 3A-3D are schematic illustrations of mating fasteners to be used with the device of FIG. 1 in accordance with some embodiments of the invention.

FIG. 3A is a schematic illustration of fasteners 340 having interlocking connections. The use of depressions-protrusion with respect to the interlocking connection is exemplary only and can be interchanged in accordance with embodiments of the invention. FIG. 3A shows two identical fasteners 340, it is noted that different fasteners having the interlocking connection described below can be used in accordance with exemplary embodiments of the invention.

Fastener 340 has a base 342 and a piercing element 344. Piercing element 344 optionally includes a tip 346 at its distal end, which is optionally sharpened and adapted to penetrate into body tissue. A cavity 348 is provided in base 342 and/or through piercing element 344, as shown in the cross-section of the fasteners in FIG. 3B.

Figure 3B:
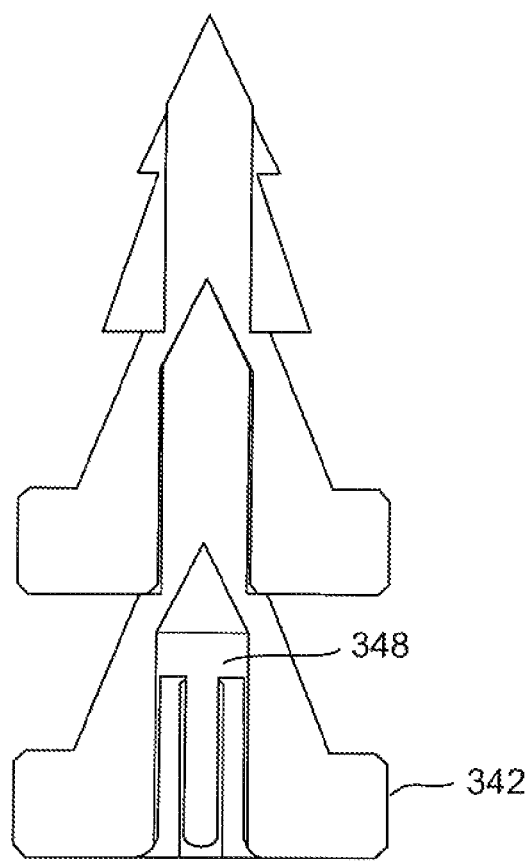

Piercing element 344 optionally includes depressions 345. Cavity 348 may include interlocking protrusions 349 formed to fit depressions 345. Thus, by connecting the fasteners 340 as shown in FIGS. 3A and 3B, the rotation of the two fasteners 340 are dependent on each other, i.e. the fasteners will either rotate at the same rate and direction together or not rotate together. When stacking the fasteners, the fasteners should be coordinated so that the protrusions will fit into the depressions in order for the fasteners to be interlocked.

However, if two connected fasteners do not have a matching cavity/piercing element (or the proximal fastener does not have a cavity at all), the rotation of one fastener will not be dependent on the rotation of the other. Thus, the two fasteners may rotate at different rates and/or directions, or one fastener may rotate while the other does not rotate. In some embodiments, a non-mating fastener will rotate in the inner tube due to friction caused by the rotating fasteners.

Figure 3C:
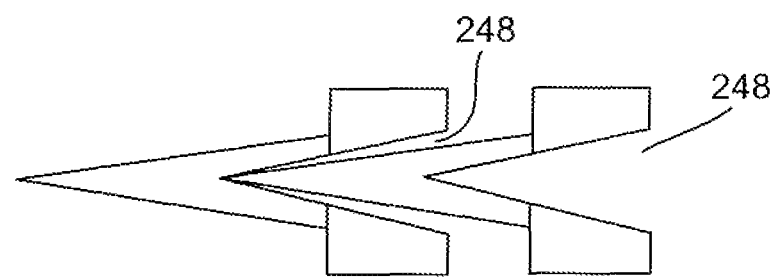

However, these fasteners will not rotate when pushed out of the tube and pierced in the body. Optionally, a non mating fastener comprises a cavity 248 which is substantially broader than the tip or piercing element of the fastener on which it is stacked, as shown in FIG. 3C, thereby reducing the friction.

Figure 3D:
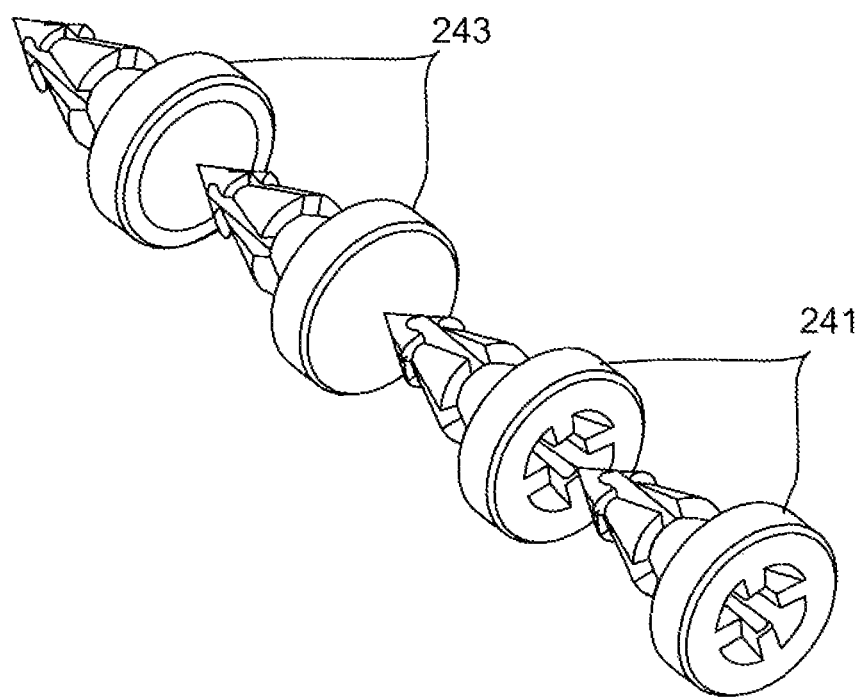

FIG. 3D illustrates four fasteners where two fasteners 241 will rotate together and two fasteners 243 will not rotate at the same rate and/or direction as fasteners 241. Fasteners 24 might in fact not rotate at all during linear displacement in the inner tube and/or out of the tube.

Figure 3E:
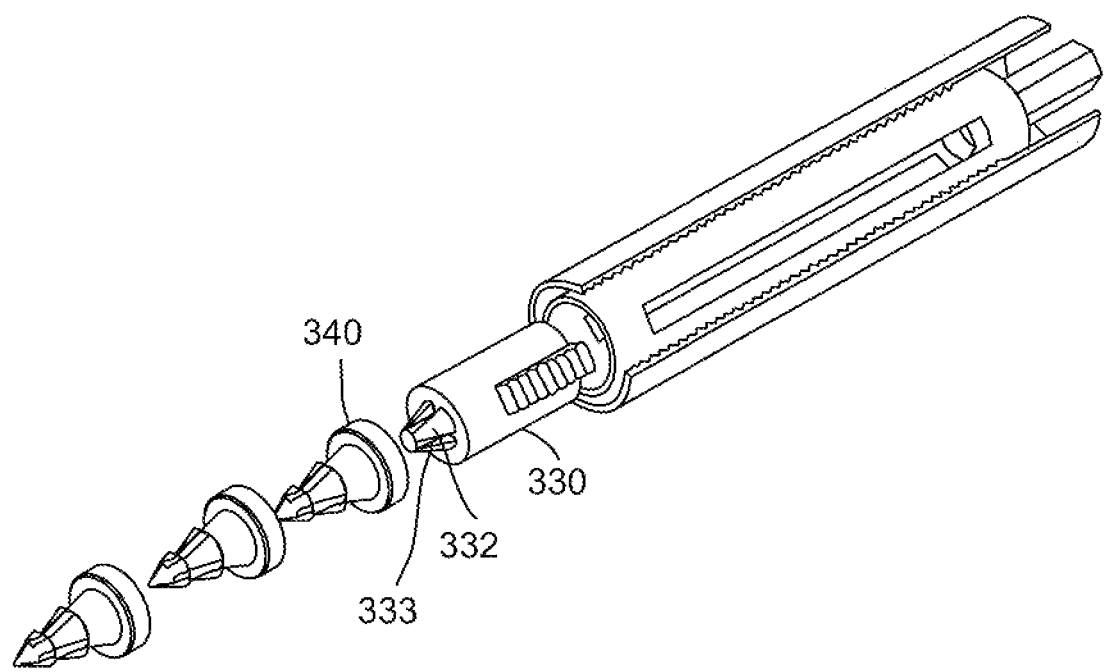
FIG. 3E is a schematic illustration of the fasteners shown in FIGS. 3A and 3B with a mating advancing element used in the device of FIG. 1A according to some embodiments of the invention.

According to some embodiments of the invention, the tip of the advancing element also comprises depressions. FIG. 3E illustrates such an advancing element 330 having a tip 332 with depressions 333. Since the advancing element rotates along with the inner tube, any fasteners having interlocking protrusions in their cavities connected in a row will rotate along with the advancing element. Fasteners having non-matching cavities, or having no cavities, stacked thereon will not rotate. In these embodiments, the surgical fastening device includes tacks and screw in an order, meaning that the fastening device will first apply tacks and then screws, unless other means causing rotation of the fasteners are provided in which case various stacking orders are possible.

FIGS. 4A-4F are schematic illustrations of an inner tube and fasteners in accordance with other embodiments of the invention enabling at least two fasteners located in the inner tube not to rotate at the same rate and/or direction.

An inner tube 420 is provided having a non-circular shaped inner cross section. FIGS. 4A-4D illustrate an inner tube with an hexagonal cross-section 422. Cross section 422 can have any other non-circular shape, for example any polygonal such as pentagonal, square, triangular or oval shaped cross section in accordance with different embodiments of the invention.

A fastener 440 is provided having a base 442 shaped to fit cross-section 422 of the inner tube, in this case a hexagonal shaped base and a threaded point which threads into body tissue like a screw.

Due to the matching base, fastener 440 will rotate along with inner tube 420 at the same rate and direction. Optionally, the fastener may have a different shape than the inner tube cross-section and still rotate with the inner tube, for example a square shaped based fastener will rotate in a rotating octagonal cross section shaped inner tube.

A fastener having a base with at least one common plane as the inner tube's cross-section will rotate with the inner tube and is referred herein as a matching base fastener.

Figure 4A:
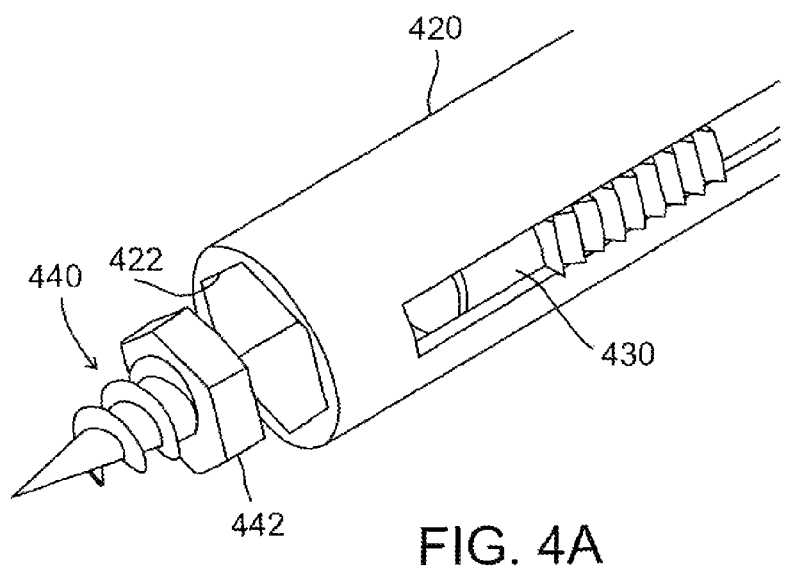
FIGS. 4A-4D are schematic illustrations of an inner tube, advancing elements and fasteners to be used with the device of FIG. 1 in accordance with some embodiments of the invention.
Figure 4B:
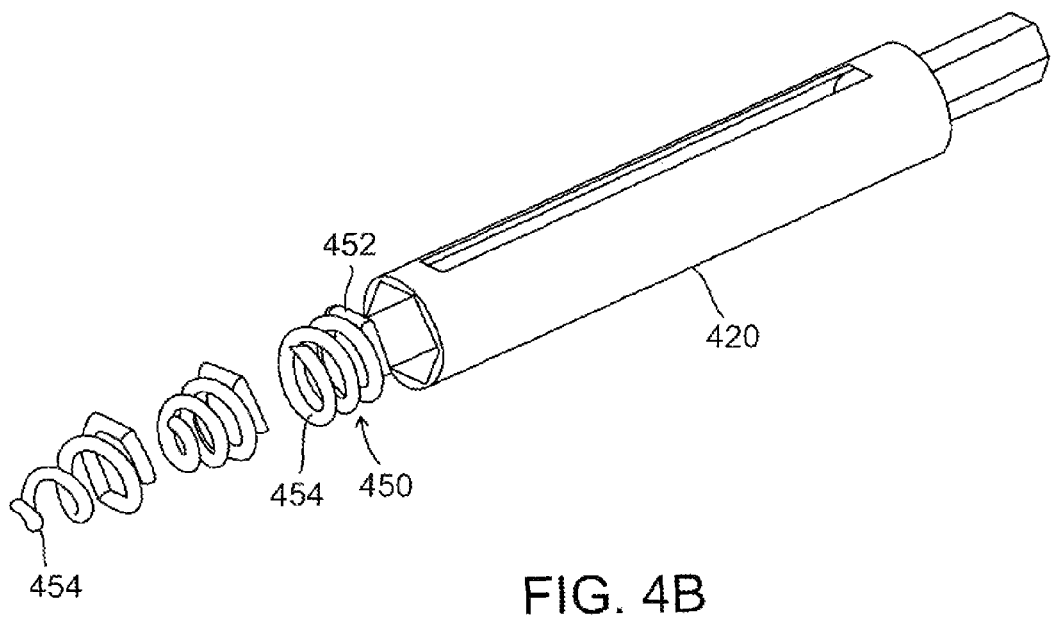

FIG. 4B is a schematic illustration of fasteners 450 made of a helical coil and having a non-circular shaped base 452 and a piercing element 454. Fasteners 450 shown have all the same base 452, hexagonally shaped to fit the cross section of the inner tube and have different piercing elements. A fastening device having an inner tube 420 can pierce the different shaped fasteners into body tissue by applying the same rotational force to inner tube 420. Optionally, the coils have a sharp distal end adapted to penetrate into body tissue.

An advancing element 430 is also provided (shown in FIG. 4A) in order to advance the fasteners linearly within inner tube 420 and out of the tube. Since advancing element 430 rotates due to its wings extended through the slots of the inner tube, advancing element 430 may have any shape that fits into the inner tube.

Optionally, some other fasteners may comprise a base having a different shape than the inner cross section of the inner tube, such that they will not rotate along with the inner tube. They may rotate at a different direction and/or rate as the inner tube or move linearly without rotation due to force provided by the advancing fasteners and/or by advancing element 430. For example, fasteners having a circular shaped base will not rotate along with a hexagonal shaped inner tube.

In this embodiment, the inner tube may comprise both matching base fasteners and non-matching base fasteners and the matching base fasteners will rotate along with the inner tube during linear displacement while the non-matching base fasteners may not rotate during linear displacement or may rotate during displacement in the inner tube due to friction at different rates and/or directions than the inner tube but will not rotate when pushed out of the tube.

Figure 4C:
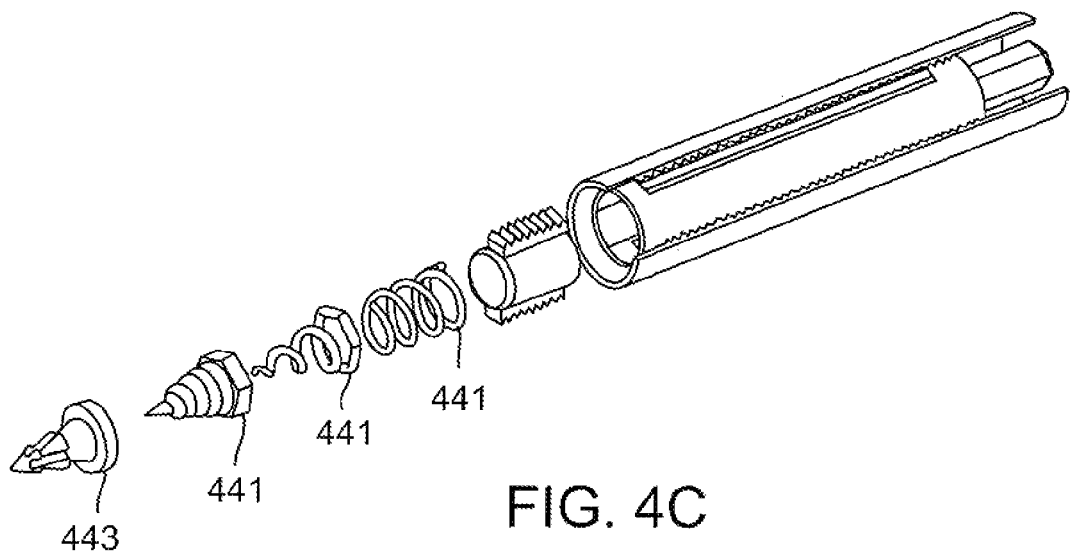

FIG. 4C is a schematic illustration of a plurality of differently based fasteners stacked in an inner tube. Fasteners 441 shown have a hexagonal shaped base and fastener 443 has a circular shaped base. Fasteners 441 are shown as screws adapted to be threaded into body tissue and fastener 443 is shown as a tack adapted to be pierced into body tissue. Screws 441 will rotate along with the inner tube having a hexagonal cross-section, while tack 443 will either rotate at a different rate and/or direction or advance linearly without rotation.

Figure 4D:
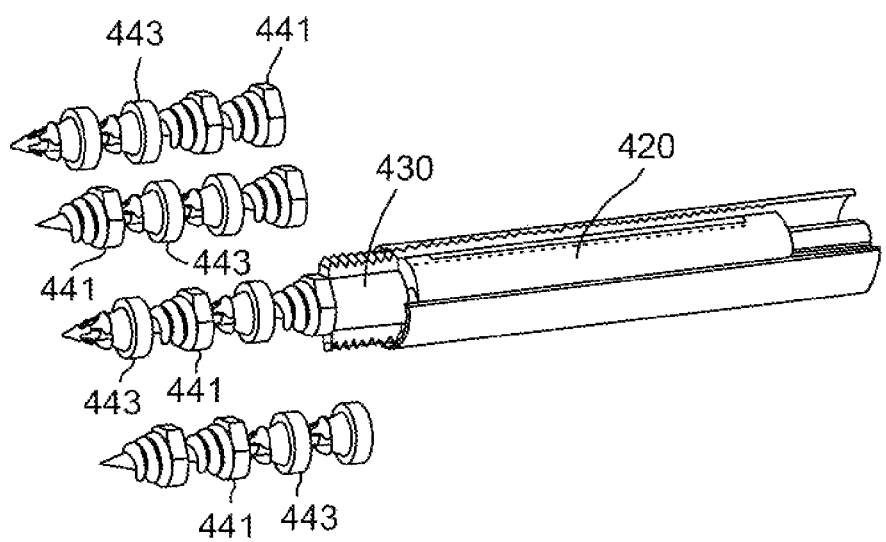

In these embodiments, the surgical fastening device can provide a mixture of screws and tacks in the inner tube and they do not need to be inserted in a certain order. FIG. 4D illustrates for example a mix of screws and tacks at different orders which are all accordance to embodiments of the present invention. The fasteners can be provided with or without cavities in their base.

According to embodiments of the present invention, a combination of the embodiments shown in FIG. 3 and the embodiments shown in FIG. 4 is provided. For example, inner tube 330 may also have a non-circular cross-section and fasteners 340 may have a base which will either match or not match the cross section of the inner tube, thereby enabling the embodiment of FIG. 3 to provide a mixture of screws and tacks which do not need to be inserted in a certain order. Optionally, fasteners 440, 441 and/or 443 comprise interlocking connectors as described with respect to FIG. 3.

Figure 4E:
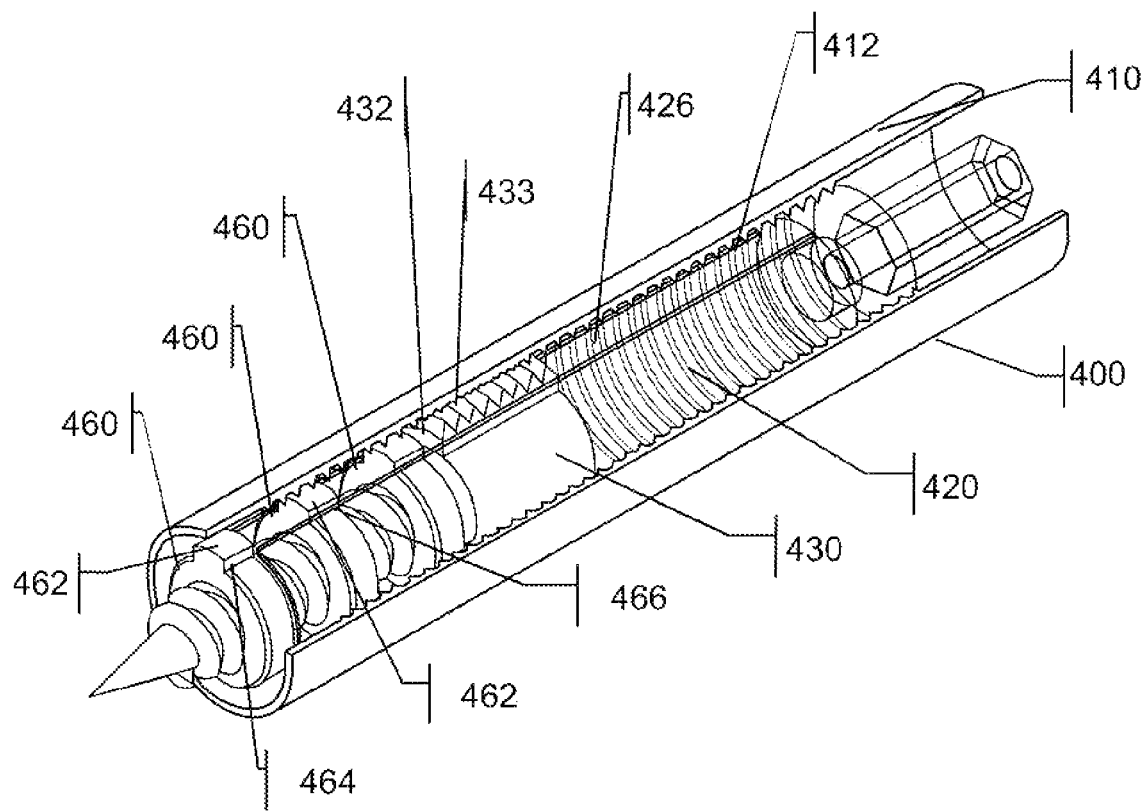
FIG. 4E is a partially cross-sectional view of an inner tube, advancing element and fasteners to be used with the device of FIG. 1 in accordance with some embodiments of the invention.

FIG. 4E illustrates an exemplary embodiment including a surgical fastening device 400 where fasteners 460 are provided with one or more wings 462 adapted to fit into slot 426 of the inner tube. Optionally, the fasteners have the same number of wings as the advancing element. Alternatively, fewer or more wings are provided. Due to positioning of the wing in the slot 426, fasteners 460 will rotate along with the inner tube. Optionally, additional fasteners (not shown) are provided without wings. In some embodiments, these additional fasteners will not rotate with the inner tube.

Optionally, the side walls 464 of wings 462, are perpendicular to the circumference of fastener 460, extending outward in a 90 degree angle from the circumference of fastener 460, and fit inside slot 426 and make contact with the surface 466 of inner tube 420 which reaches to slot 426, interfering with the rotation of the fastener. Alternatively, side walls 464 extend out from the circumference of fastener 460 at an angle less than 90 degrees between side wall 464 and the part of the circumference of fastener 460 which is outside of wing 462, so that the front and back walls of wing 462 are broader distally than proximally to the fastener.

Optionally, surgical fastening device 400 has a circular shaped inner tube 420 where some of the fasteners may rotate during linear advancement while others may not rotate. An advancing element 430 comprises at least one threaded wing 432 and fits into inner tube 420, such that threads 433 on wing 432 extend out of at least one slot 426 and are threaded into inner threads 412 of outer tube 410. Optionally, slot 426 extends to the distal end of inner tube 420.

Figure 4F:
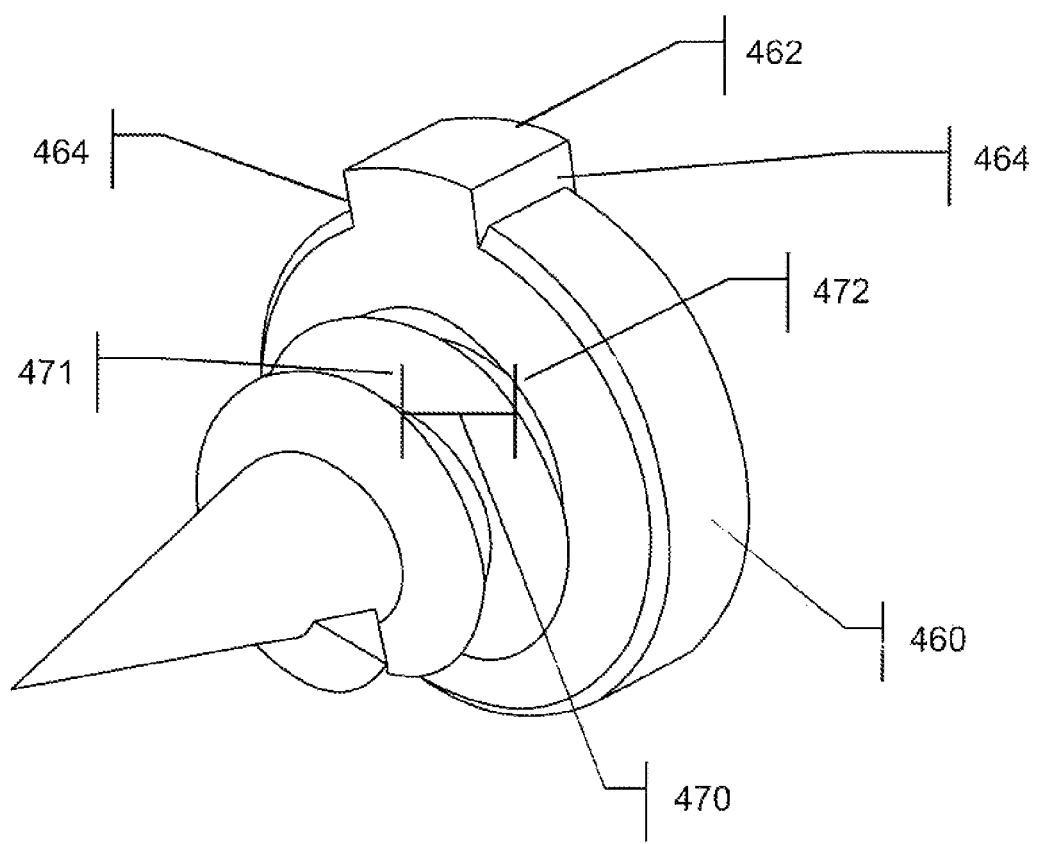
FIG. 4F is a schematic illustration of the fastener used in the device of FIG. 4E according to some embodiments of the invention.

FIG. 4F is a schematic illustration of fastener 460 used in device 400 from FIG. 4E with one protrusion 462 comprising side walls 464 which are perpendicular to the circumference of fastener 460, extending outward in a 90 degree angle from the circumference of fastener 460. Optionally, the number of protrusions is one or two. Optionally there are more than two protrusions.

Optionally, where there is a plurality of protrusions, the protrusions are of the same shape. Alternatively, the protrusions are not of the same shape. Optionally, the protrusions are of the same size. Alternatively, the protrusions are not of the same size. Optionally, the protrusions are equidistant from each other around the circumference. Alternatively, the protrusions are not equidistant from each other. Optionally, the protrusions are positioned so as to be symmetrical between one half of the circumference of the fastener and the other half. Alternatively, the protrusions are positioned so as not to be symmetrical. The different positions of the protrusions may provide different levels of strength, rigidity and/or stability. The differences in the shapes of the protrusions lead to different alignments of the fasteners once the protrusions are matched with corresponding slots in the inner tube. The alignment of the fasteners may be useful to dictate where the position of the beginning of the thread located on the fastener.

The desired threading position and level of strength, rigidity and/or stability of the fastener may depend on the particular object being fastened, so that different positions of protrusions may be advantageous for the fastening of different objects.

In some embodiments of the invention, the fasteners 460 are threaded. In some embodiments, the pitch of the thread to the fastener is constant. That is, the distance 470 between point 471 on the distal thread and point 472, located at the same point of the circumference of the proximal thread as point 471, will be constant wherever measured.

In some embodiments, the pitch of the thread to the fastener is variable. In some embodiments, once fastener threads engage tissue the fastener threads cause the fastener on which they are threaded to advance at a speed different than the speed at which the device pushes the fastener.

For example, the pitch of the thread to the fastener may be greater than the pitch of the shaft. This may be useful when implanting objects for which it is beneficial to advance the objects more quickly than the progression of the advancing element once the object enters the body.

In another example, the pitch of the thread to the fastener may be equal to the pitch of the shaft. This may be useful when implanting objects for which it is beneficial to advance the objects at a rate equal to the progression of the advancing element once the object enters the body.

In another example, the pitch of the thread to the fastener may be less than the pitch of the shaft. This may be useful when implanting objects for which it is beneficial to advance the objects more slowly than the progression of the advancing element once the object enters the body.

Figure 5A:
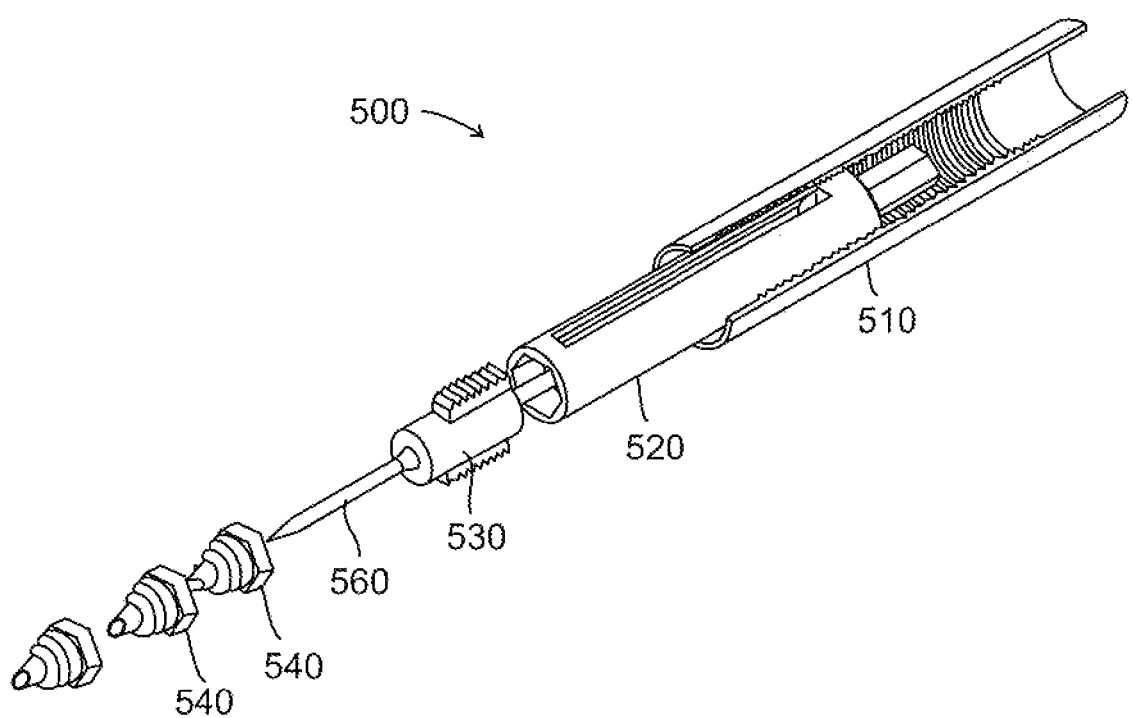
FIG. 5A is an exploded view of a fastening device comprising a shaft in accordance with some embodiments of the invention.
Figure 5B:
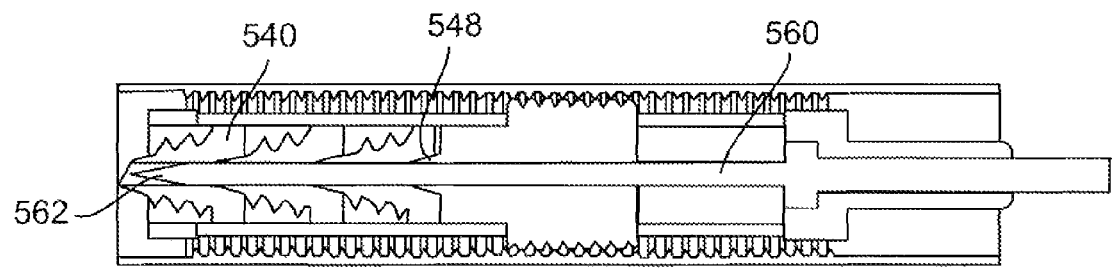
FIG. 5B is a cross-sectional view of the device shown in FIG. 5A according to some embodiments of the invention.
Figure 5C:
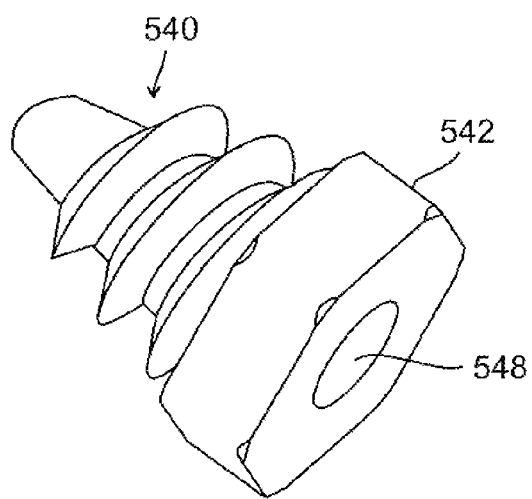
FIG. 5C is a schematic illustration of a fastener used in the device of FIG. 5A according to some embodiments of the invention.

FIG. 5A is a schematic elaborated view of a surgical fastening device 500 comprising a shaft 560 around which fasteners 540 and advancing mechanism 530 are positioned. FIG. 5B is a cross-section of a fastening device comprising a shaft 560 in accordance with exemplary embodiments of the invention. FIG. 5C is a schematic illustration of a fastener 540 showing a bore 548 passing throughout fastener 540, whereby fastener 540 is made hollow and adapted to be fitted onto shaft 560. Bore 548 may have male protrusions or female depressions as described with respect to FIG. 3. Similarly, fastener 540 may have a shaped base as described with respect to FIG. 4.

Fastening device 500 further comprises an inner tube 520, an outer tube 510 and operates similarly to the embodiments described with respect to FIGS. 1-4 above.

The outer surface of the shaft may be smooth and does not require any threads, incisions or protrusions on its outer surface. Optionally, the outer surface of the shaft is smooth along at least 50%, 60%, 80% or 90% of the length of the shaft.

In some embodiments, shaft 560 comprises a needle having a sharpened distal end 562 for piercing into body tissue. Optionally, fasteners 540 comprise no sharpened end and end 562 assists in piercing the fasteners into body tissue. Optionally, shaft 560 is relatively thin, for example less than 1 mm in diameter, and is adapted to penetrate into body tissue without sharpened end.

In some embodiments, shaft 560 is static and does not move relative to the inner and outer tube. Optionally, shaft 560 can move linearly along the length of the inner tube in order to pierce into body tissue. Alternatively or additionally, the shaft rotates along its axis. The movement of shaft 560 is independent of the movement of fasteners 540, i.e. the fasteners may move while the shaft is static and the shaft may move while the fasteners are static, or both may move and/or rotate in different directions and/or at different rates or in the same directions and/or at the same rates.

Figure 5D:
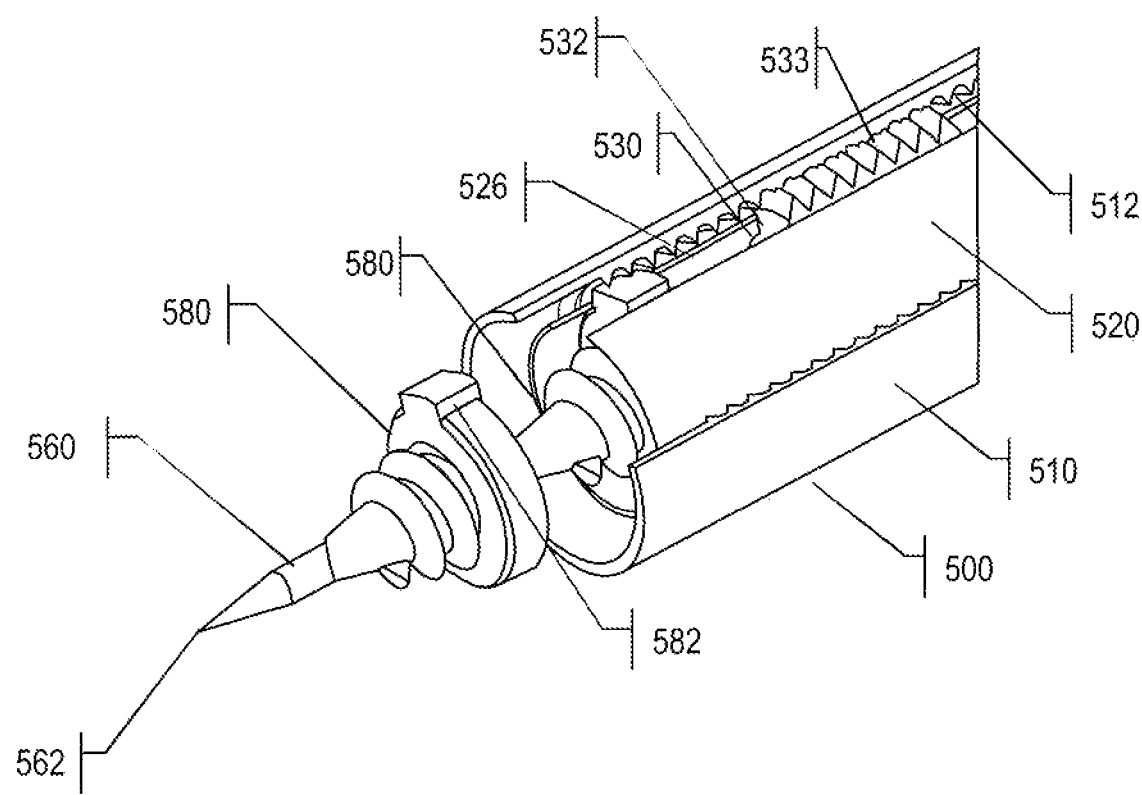
FIG. 5D is a partially cross-sectional view of the distal end of the device of FIG. 5A with a fastener according to another embodiment of the invention.

FIG. 5D is a schematic elaborated view of a surgical fastening device 500 comprising advancing element 530 comprising an internal hollow space, creating a bore along its length. Optionally, shaft 560 is fitted to go through the bore of the advancing element. Optionally, the shaft fitted to go through the bore comprises a needle having a sharpened distal end 562.

In an exemplary embodiment, at least one fastener 580 is positioned around shaft 560 and contains at least one wing 582. Fasteners 580 can be similar to fasteners 460 described with respect to FIGS. 4E and 4F above, except that they are made hollow. Optionally, fastener 580 comprises an internal hollow space, creating a bore along its length. Optionally, shaft 560 is fitted to go through the bore of the fastener 580. Optionally, the shaft fitted to go through the bore comprises a needle having a sharpened distal end 562.

In an exemplary embodiment, an advancing element 530 comprises at least one threaded wing 532 and fits into inner tube 520, such that threads 533 on wing 532 extend out of at least one slot 526 and are threaded into inner threads 512 of outer tube 510.

Optionally, the rotation of the threads is opposite to the rotation of the advancing element causing the fastener to move in the opposite direction of the advancing element after the fastener contacts body tissue. Optionally, the inner tube is threaded so as to cause the fastener to move in the opposite direction of the advancing element even before the fastener contacts body tissue.

In an exemplary embodiment, shaft 560 linearly advances toward body tissue so that sharpened distal end 562 pierces into body tissue the wings of advancing element 530 are threaded into inner threads 512 of outer tube 510. Advancing element 530 linearly advances and pushes fastener 580 distally out of inner tube 520 and into body tissue. Fastener 580 may rotate at the same rate as the inner tube, rotate at a different rate and/or direction, or not rotate during linear advancement and penetration into body tissue, as for example described with respect to FIGS. 3 and 4 above. Shaft 560 may then be linearly retracted so as to withdraw out of body tissue and fastening device 500 may be removed out of the body or moved to a different location along body tissue for introducing one or more additional fasteners.

Figure 5E:
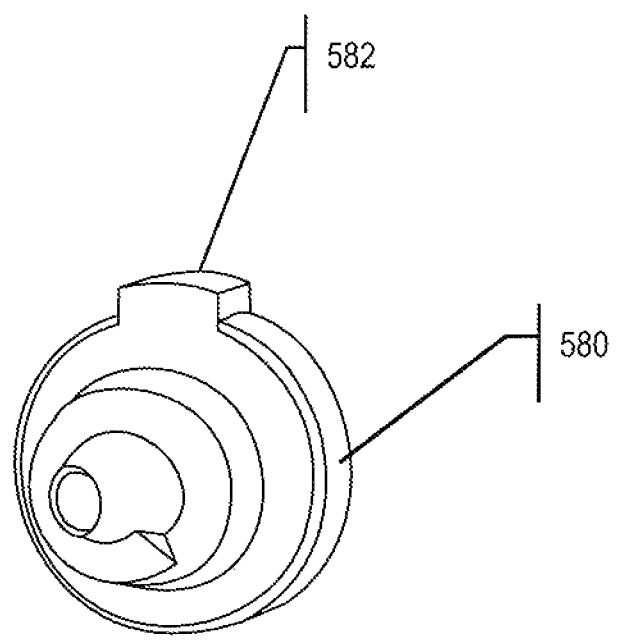
FIG. 5E is a schematic illustration of the fastener used in the device of FIG. 5D according to some embodiments of the invention.

FIG. 5E is a schematic illustration of fastener 580 used in device 500 from FIG. 5D containing a wing 582.

Figure 5F:
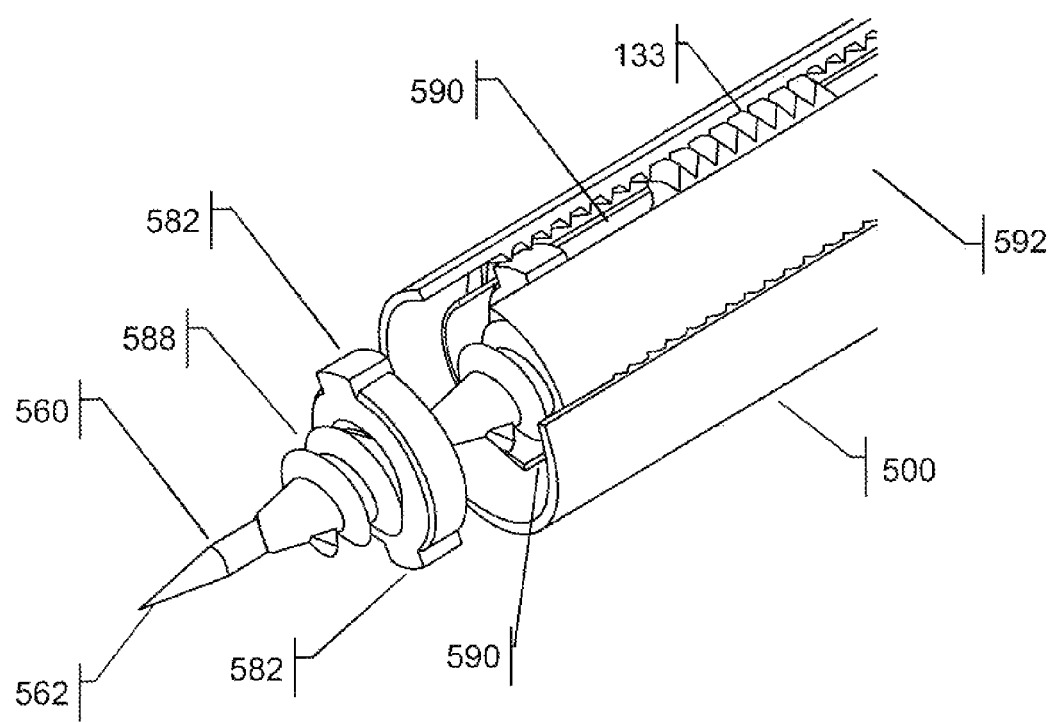
FIG. 5F is a partially cross-sectional view of the device of FIG. 5A with a fastener according to yet another embodiment of the invention.

The fasteners may comprise more wings, depending, for example, on the number of slots provided in the inner tube. Optionally, the fasteners may comprise fewer wings than the number of slots provided in the inner tube. For example, FIG. 5F illustrates another exemplary embodiment where a schematic elaborated view of a surgical fastening device 500 comprising a shaft 560 around which are positioned fasteners 588, each having two wings 582, is provided. In an exemplary embodiment, fasteners 580 are positioned around shaft 560.

Optionally, the advancing element (not seen) comprises an internal hollow space, creating a bore along its length. Optionally, shaft 560 is fitted to go through the bore of the advancing element. Optionally, the shaft fitted to go through the bore comprises a needle having a sharpened distal end 562.

Optionally, at least one fastener 588 comprises an internal hollow space, creating a bore along its length. Optionally, the shaft 560 is fitted to go through the bore of the fastener 588. Optionally, the shaft 560 fitted to go through the bore comprises a needle having a sharpened distal end 562.

As noted above, where there is a plurality of protrusions, the protrusions may be of same or different shapes, and/or symmetrically and/or equidistantly arranged. These differences may be used to provide desired levels of strength, rigidity and/or stability and/or to control relative alignment of the fastener and inner or outer tube.

In some embodiments of the invention, the fasteners 460 are threaded. In some embodiments, the pitch of the thread to the fastener is constant. That is, the distance 470 between point 471 on the distal thread and point 472, located at the same point of the circumference of the proximal thread as point 471, will be constant wherever measured.

As noted above, the pitch may be variable or fixed and/or may match or not the pitch of the advancing element, so as to optionally provide a difference in linear motion.

In general, features shown in one embodiment (such as wings or shaft) may be used in other embodiments. Specifically however, optional features regarding threading, protrusion and/or wing design, inner tube, fastener and/or shaft geometry, advancing element design and/or fastener arrangement may be applied to various of the embodiments described herein.

Figure 5G:
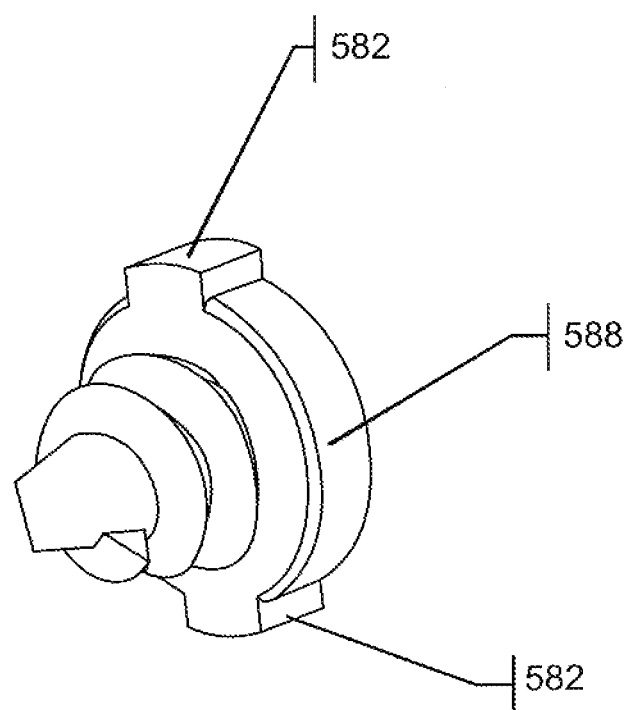
FIG. 5G is a schematic illustration of the fastener used in the device of FIG. 5F according to some embodiments of the invention.

FIG. 5G is a schematic illustration of fastener 588 from FIG. 5F having two wings 582 which are fitted into two slots 590 in the inner tube.

In some embodiments of the invention, the fasteners 588 are threaded.

Other shapes of the inner tube may be provided in accordance with exemplary embodiments of the invention. The embodiments below are shown with a shaft but can operate without a shaft in accordance with embodiments of the invention.

Figure 5H:
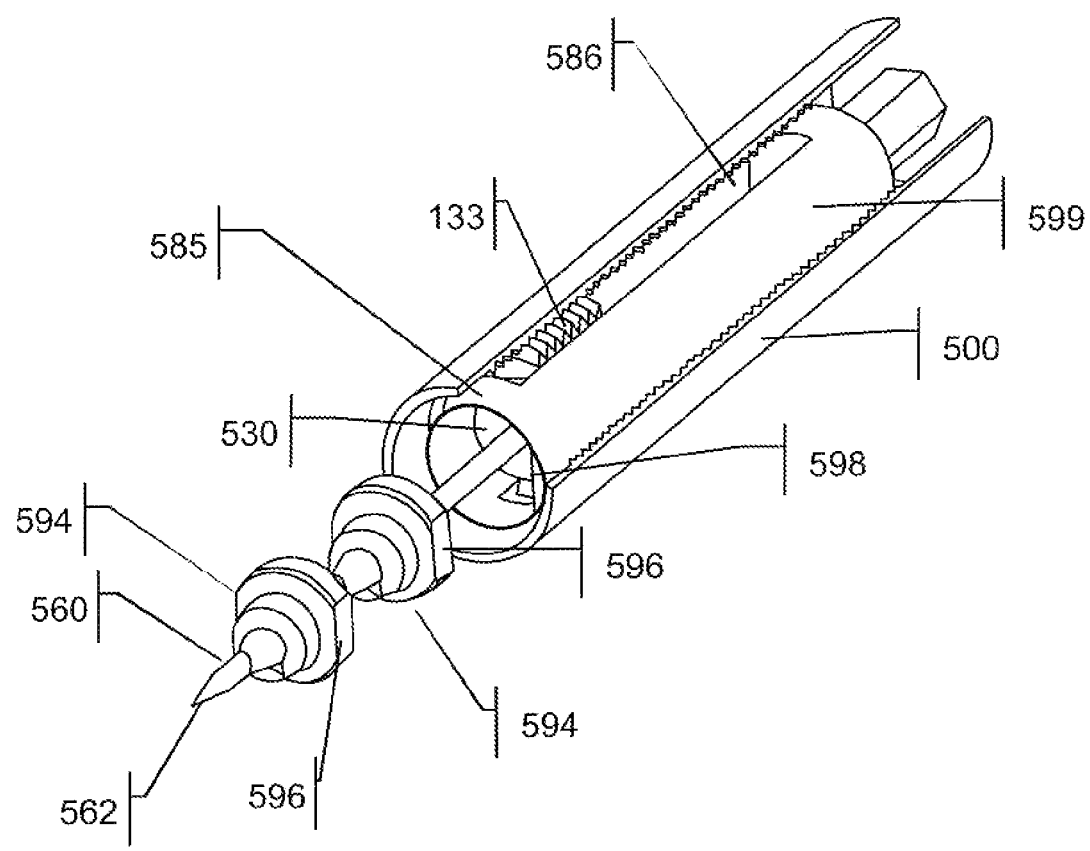
FIG. 5H is a partially cross-sectional view of a fastening device comprising a shaft according to another embodiment of the invention.

For example, FIG. 5H illustrates an exemplary embodiment where a schematic elaborated view of a fastening device 500 wherein inner tube 599 comprises a circular shaped cross-section with a non-constant diameter and wherein at least one fastener 594 comprises a circular shaped base having a non-constant diameter fitted to inner tube 599. In some embodiments, two fasteners 594 are positioned around shaft 560. One fastener 594 contains a flat or nearly flat side 596 which is fitted to the flat or nearly flat side 598 of inner tube 599. Optionally, the circular shaped cross-section with a non-constant diameter contains a geometry other than a flat or nearly flat side.

In some embodiments, inner tube 599 contains at least one longitudinal slot 586 that does not extend to the distal end of the inner tube and/or also does not extend to the proximal end of the inner tube, instead forming a bridge 585 at the distal end and/or in addition to the bridge at the proximal end of the inner tube. Flat or nearly flat side 598 is located on bridge 585, which optionally provides increased strength, rigidity and/or stability to the fastening device, which may be advantageous for the fastening of certain objects.

Optionally, the advancing element 530 comprises an internal hollow space, creating a bore along its length. Optionally, shaft 560 is fitted to go through the bore of the advancing element. Optionally, the shaft fitted to go through the bore comprises a needle having a sharpened distal end 562.

Optionally, at least one fastener 594 comprises an internal hollow space, creating a bore along its length. Optionally, the shaft is fitted to go through the bore of the fastener 594. Optionally, the shaft 560 fitted to go through the bore comprises a needle having a sharpened distal end 562.

Figure 5I:
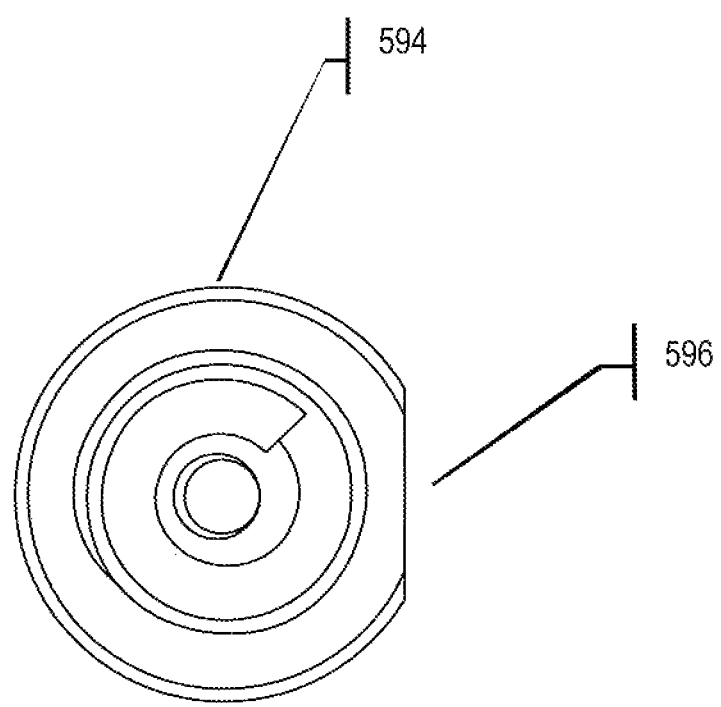
FIG. 5I is a front view of a fastener used in the device of FIG. 5H according to some embodiments of the invention.

FIG. 5I is a schematic illustration of fastener 594 from FIG. 5H containing a flat side or nearly flat side 596.

In operation, the rotation, or lack of rotation, of fasteners 594 will match the rotation, or lack of rotation, of inner tube 599 due to their matching bases and will be independent of the rotation, or lack of rotation, of the advancing element 530 Although not shown, inner tube 599 may include fasteners with other shaped bases which will not rotate along with the inner tube, for example circular based fasteners with smaller cross-section.

Figure 5J:
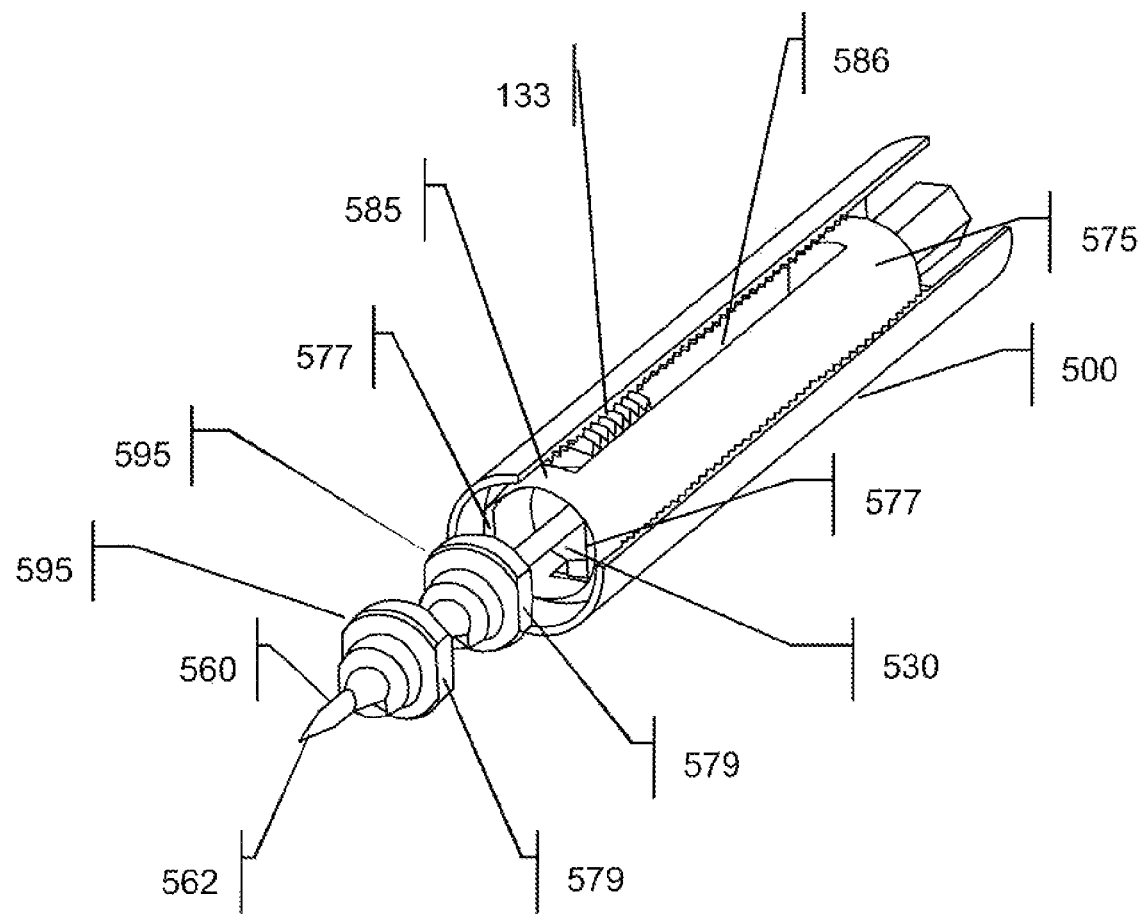
FIG. 5J is a partially cross-sectional view of a fastening device comprising a shaft according to another embodiment of the invention.

FIG. 5J illustrates an exemplary embodiment where a schematic elaborated view of a surgical fastening device 500 comprising inner tube 575 having two flat or nearly flat sides 577 is provided. Two fasteners 595 are positioned around a shaft 560. The fasteners 595 comprise a circular shaped base with two flat or nearly flat sides 579 which fit into and correspond to two flat or nearly flat sides of the inner tube. Optionally, the number of flat or nearly flat sides is more than two.

Optionally, where there is a plurality of areas along the cross-section of the fasteners with a non-constant diameter, the areas with a non-constant diameter are of the same geometry. Alternatively, the areas with a non-constant diameter are not of the same geometry. The different geometries provide different levels of strength, rigidity and/or stability. The desired level of strength, rigidity and/or stability may depend on the particular object being fastened, so that different geometries of protrusions are advantageous for the fastening of different objects.

Optionally, the areas with a non-constant diameter are equidistant from each other. Alternatively, the areas with a non-constant diameter are not equidistant from each other. Optionally, the areas along the cross-section of the fasteners with a non-constant diameter are positioned so as to be symmetrical between one half of the circumference of the fastener and the other half. Alternatively, the areas along the cross-section of the fasteners with a non-constant diameter are positioned so as not to be symmetrical. The different positions provide different levels of strength, rigidity and/or stability. The desired level of strength, rigidity and/or stability may depend on the particular object being fastened, so that different positions of areas with a non-constant diameter are advantageous for the fastening of different objects.

In some embodiments, inner tube 575 contains at least one longitudinal slot 586 that does not extend to the distal end of the inner tube and also does not extend to the proximal end of the inner tube, instead forming a bridge 585 at the distal end in addition to the bridge at the proximal end of the inner tube. Flat or nearly flat sides 577 are optionally located on bridge 585, which may provide increased strength, rigidity and/or stability to the fastening device, which is advantageous for the fastening of certain objects. Similarly, where the inner tube is grooved, such grooves are optionally avoided at the bridge.

Optionally, the advancing element 530 comprises an internal hollow space, creating a bore along its length. Optionally, shaft 560 is fitted to go through the bore of the advancing element. Optionally, the shaft fitted to go through the bore comprises a needle having a sharpened distal end 562.

Optionally, at least one fastener 595 comprises an internal hollow space, creating a bore along its length. Optionally, the shaft 560 is fitted to go through the bore of the fastener 595. Optionally, the shaft 560 fitted to go through the bore comprises a needle having a sharpened distal end 562.

Figure 5K:
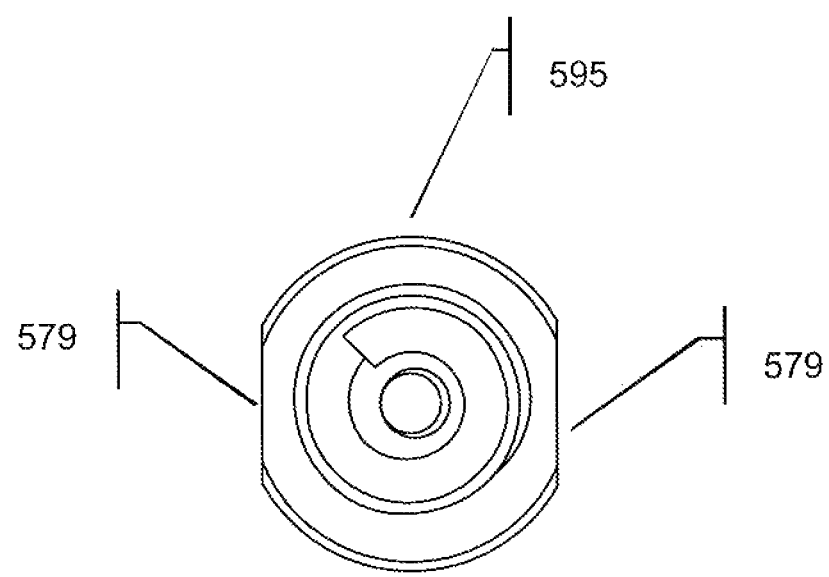
FIG. 5K is a schematic illustration of the fastener used in the device of FIG. 5J according to some embodiments of the invention.

FIG. 5K is a schematic illustration of a fastener 595 from FIG. 5J containing two flat or nearly flat sides 579.

Figure 5L:
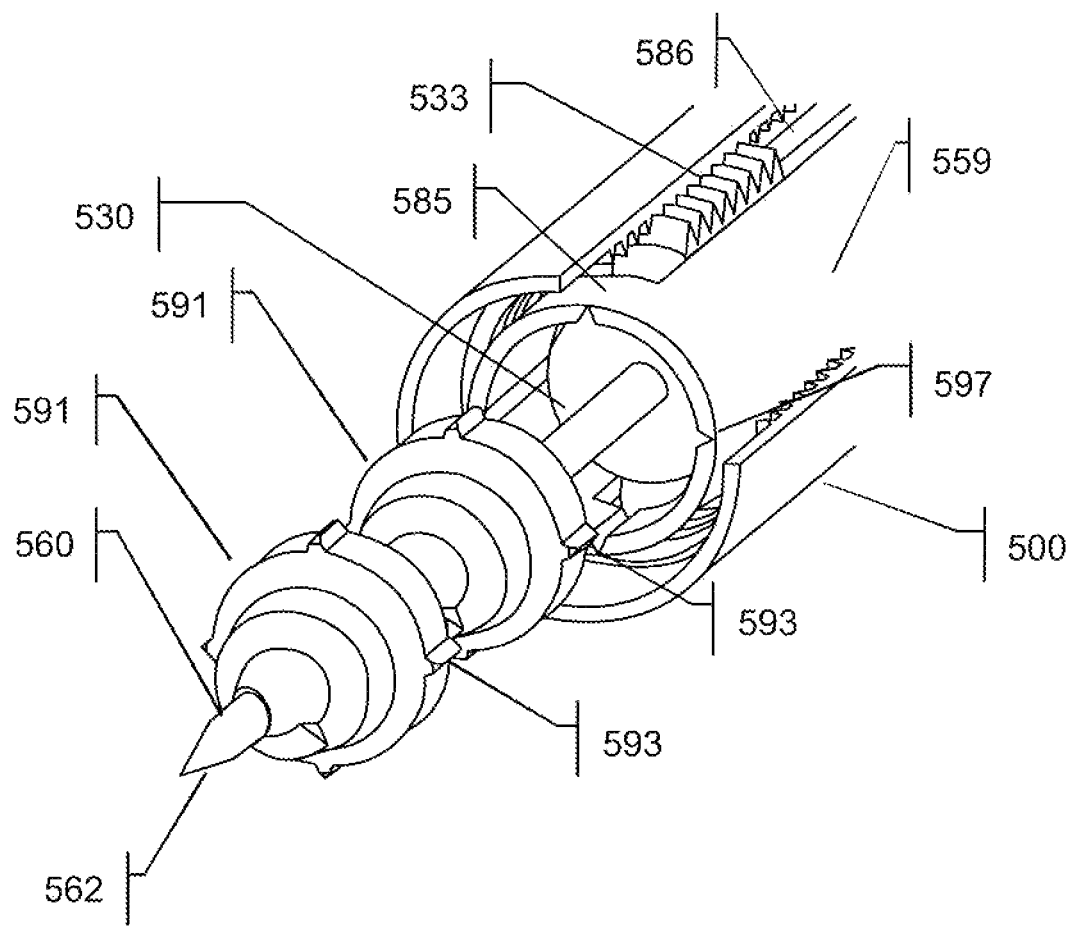
FIG. 5L is a partially cross-sectional view of a fastening device comprising a shaft according to another embodiment of the invention.

According to other embodiments of the invention, the inner tube may comprise a circular inner shape with one or more indents. For example, FIG. 5L illustrates an exemplary embodiment where a schematic elaborated view of a surgical fastening device 500 comprising inner tube 559 having a circular inner shape with one or more indents 597 is provided. Two fasteners 591 are positioned around shaft 560. The fasteners 591 comprise a circular shaped base with one or more protrusions 593 which fit into indents 597 of the inner tube 559. Optionally, the indents of the inner tube 559 and corresponding protrusions 593 of the fasteners 591 are triangular or nearly triangular shaped. Alternatively, the indents and corresponding protrusions have a geometry other than triangular. Optionally, the number of triangular or nearly triangular protrusions is four. Optionally there are more or less than four triangular or nearly triangular protrusions.

In some embodiments, inner tube 559 contains at least one longitudinal slot 586 that does not extend to the distal end of the inner tube and also does not extend to the proximal end of the inner tube, instead forming a bridge 585 at the distal end in addition to the bridge at the proximal end of the inner tube. Indents 597 are optionally positioned on bridge 585 which may provide increased strength, rigidity and/or stability to the fastening device, which is advantageous for the fastening of certain objects.

At least one fastener 591 is made hollow for receiving a shaft 560 comprising a needle having a sharpened distal end 562.

Optionally, the advancing element 530 comprises an internal hollow space, creating a bore along its length. Optionally, shaft 560 is fitted to go through the bore of the advancing element. Optionally, the shaft fitted to go through the bore comprises a needle having a sharpened distal end 562.

Optionally, at least one fastener 591 comprises an internal hollow space, creating a bore along its length. Optionally, the shaft 560 is fitted to go through the bore of the fastener 591. Optionally, the shaft 560 fitted to go through the bore comprises a needle having a sharpened distal end 562.

Figure 5M:
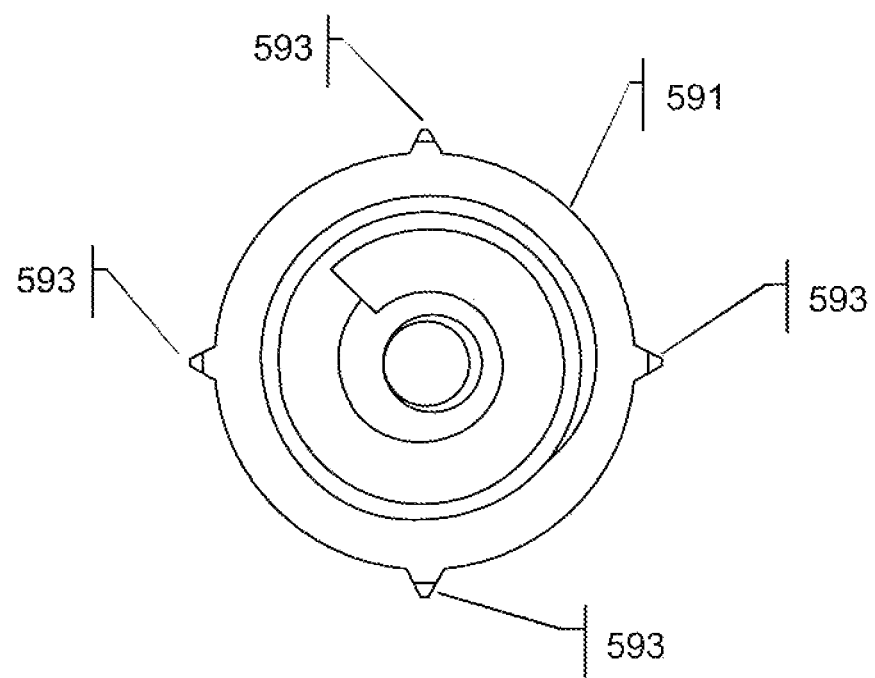
FIG. 5M is a schematic illustration of the fastener used in the device of FIG. 5L according to some embodiments of the invention.

FIG. 5M is a schematic illustration of fastener 591 from FIG. 5L containing protrusions 593. The fasteners may comprise more wings, depending on the number of slots provided in the inner tube. Optionally, the fastener may contain fewer protrusions than the number of indents in the inner tube.

In an exemplary embodiment of the invention, the protrusions fitted into the indents cause the fasteners to have a rotation or lack of rotation matching that of inner tube 559 and not with advancing element 530. Optionally, additional fasteners (not shown) are provided without protrusions. These additional fasteners will not rotate along with the inner tube. In some embodiments of the invention, the fasteners 591 are threaded.

Figure 6:
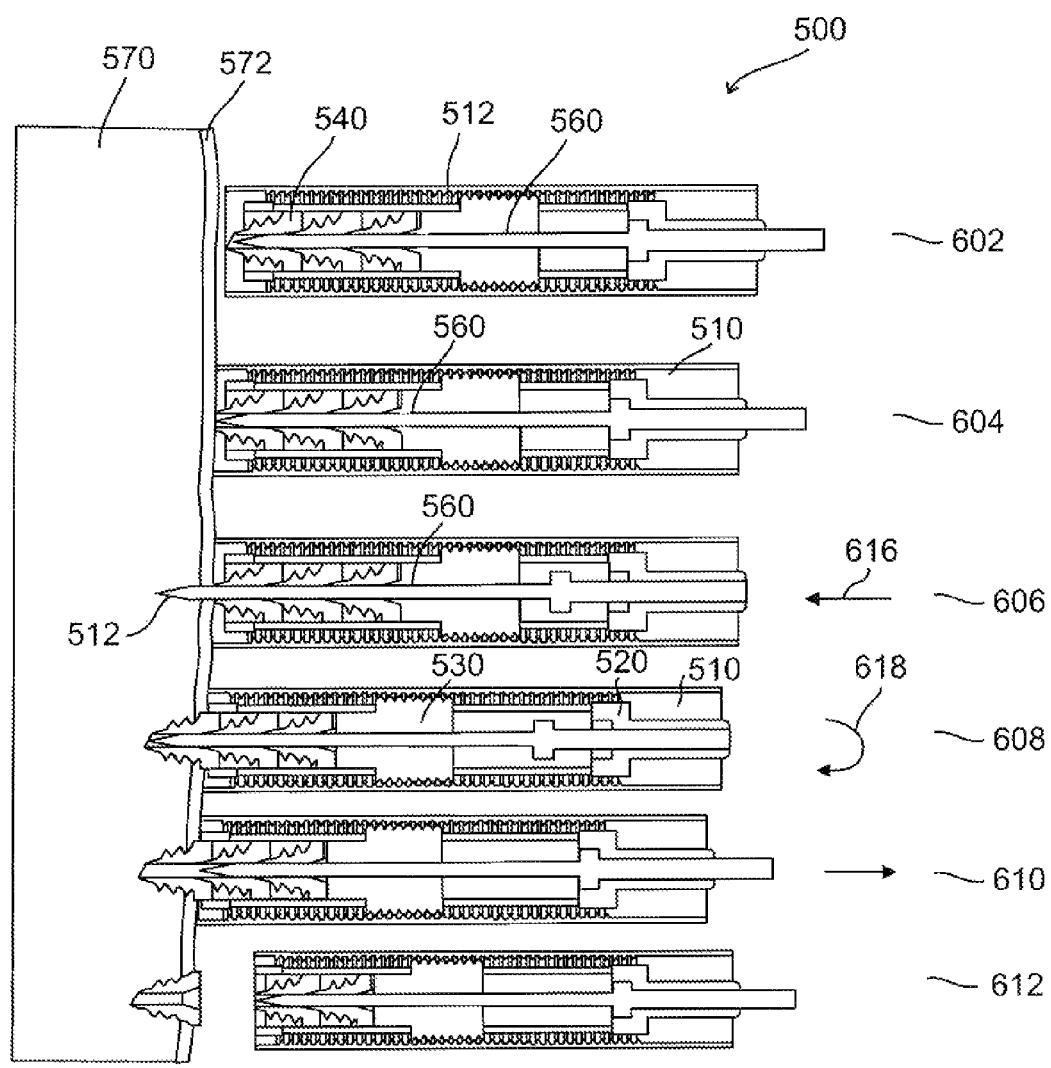
FIG. 6 provides cross-sectional views illustrating the fastening device of FIG. 5 during the stages of piercing a fastener into body tissue.

FIG. 6 provides cross-sections of fastening device 500 during the stages of piercing a fastener 540 through a mesh 572 into body tissue 570 for attaching the mesh to the body tissue. Mesh 572 is exemplary only and may be any material or medical device known in the art, for example slings, hernia support materials, organ support materials or sutures. In addition, body tissue 570 may comprise soft tissues, ligaments or bones according to exemplary embodiments of the invention.

At 602 fastening device 500 is introduced into the body of a living being. At 604 fastening device 500 is brought into contact with body tissue 570. At 606, needle 560 linearly advances in a direction 616 so that needle point 562 pierces into body tissue 570. Inner tube, advancing element and fasteners remain static during advancement of the needle. At 608, inner tube 520 rotates in a direction 618 so that the wings of advancing element 530 are threaded into inner threads 512 of outer tube 510. Advancing element 530 thereby linearly advances and pushes fastener 540 distally out of inner tube 520 and into body tissue 570. Fastener 540 may either rotate at the same rate as the inner tube, rotate at a different rate and/or direction, or not rotate during linear advancement and penetration into body tissue, as for example described with respect to FIGS. 3 and 4 above. Needle 560 is then linearly retracted at 610 so as to withdraw out of body tissue 570. At 612, fastening device 500 may be removed out of the body or moved to a different location along body tissue 570 for introducing one or more additional fasteners.

In some embodiments of the invention, shaft or needle 560 is fixed and does not move with respect to other elements of fastening device 500. The fixed position of the needle is such that the needle point extends out of the inner tube and adapted to be pierced into body tissue. In some embodiments of the invention, securing means are provided securing the needle point from unintentional damaging tissue during its travel in the body till the tissue to be penetrated is reached. FIGS. 7 and 8 illustrate such exemplary securing means. Other securing means known in the art may be provided.

Figure 7A:
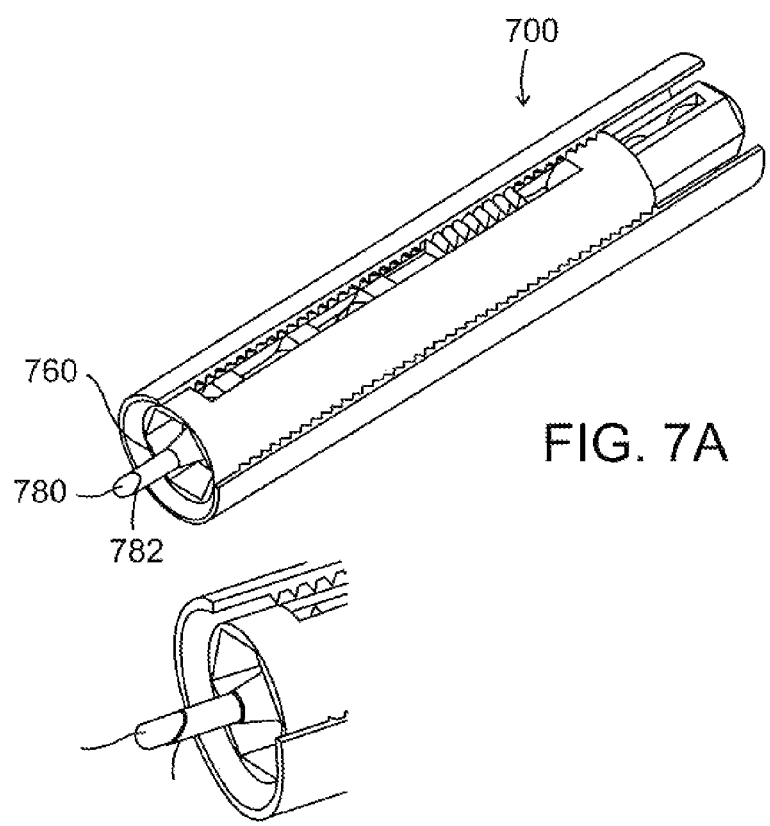
FIG. 7A is a schematic illustration of a fastening device comprising securing means in accordance with some embodiments of the invention.
Figure 7B:
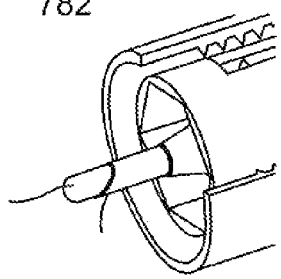
FIG. 7B is a magnified view of the distal section of the device of FIG. 7A.
Figure 7C:
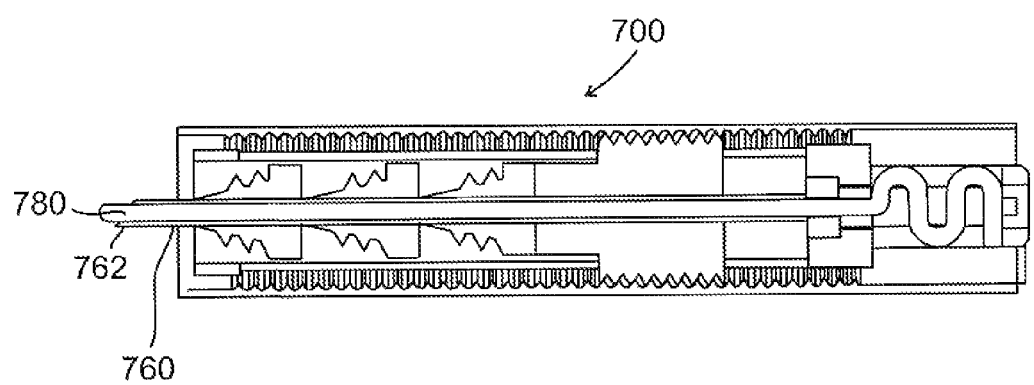
FIG. 7C is a cross-sectional view of the device of FIG. 7A in accordance with some embodiments of the invention.

FIG. 7A is a schematic illustration of a fastening device 700. FIG. 7B is a magnified view of the distal end of device 700. FIG. 7C is a cross-sectional view of device 700 showing the elements in the device. Device 700 is similar to device 500 described with respect to FIG. 5, except that needle 560 is replaced with a hollow needle 760. An inner shaft 780 is inserted within the hollow needle such that shaft 780 extends out of needle when no force is applied to it and thereby secures non-target body tissue from needle point 760.

Shaft 780 includes a spring 782 which retracts when force is applied to the distal end of shaft 780, for example when fastening device is pushed against body tissue, thereby retracting inner shaft into needle 760 and exposing needle end 762. Spring 782 can be located at the narrow proximal portion of the inner tube as shown in FIG. 7A or at any other location along needle 760. Shaft may therefore be as long as the needle, shorted or longer.

Figure 7D:
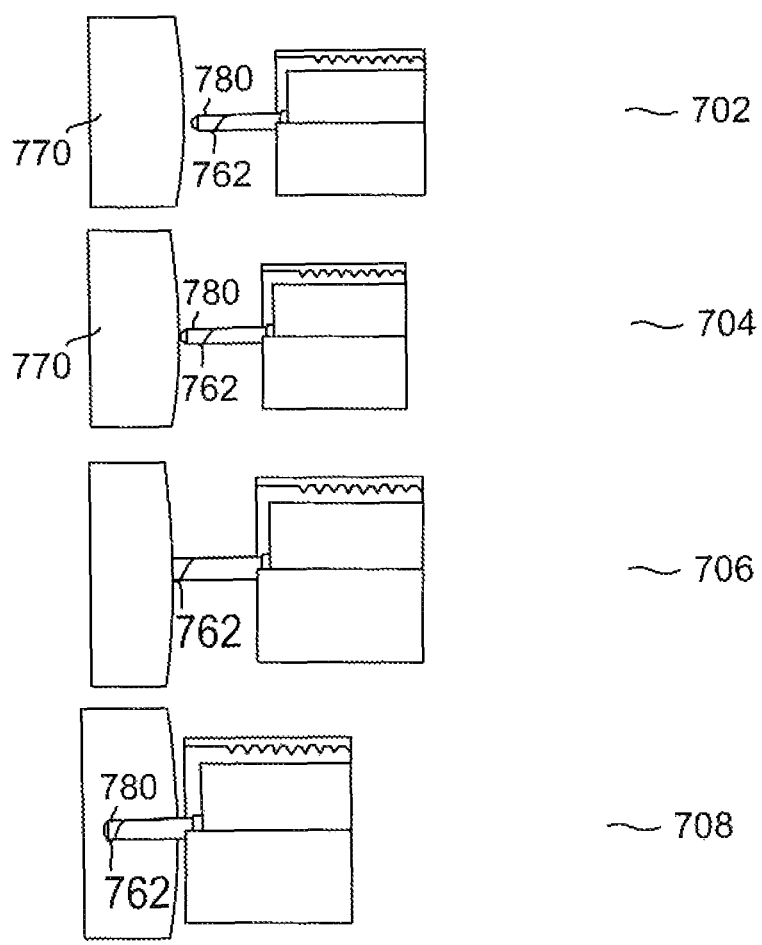
FIG. 7D schematically illustrates the distal end of the fastening device of FIG. 7A at the stages of piercing a needle point into body tissue.

FIG. 7D illustrates the distal end of fastening device 700 at the stages of piercing needle point 762 through mesh 772 into body tissue 770. Mesh 772 and tissue 770 are exemplary only and may be replaced with the examples provided with respect to mesh 572 and tissue 570 above. Fastening device 700 is introduced into a body of a living being at 702 and brought into proximity of body tissue 770 at 704. During these stages, needle end 762 is not exposed and is secured by the distal end of shaft 780. At 706, fastening device 700 is pushed against tissue 770, thereby causing spring 782 (not shown) to contract and shaft 780 to retract inwardly into needle 760. Needle end 762 is thereby exposed. At 708, needle end 762 penetrates into body tissue 770.

Figure 8A:
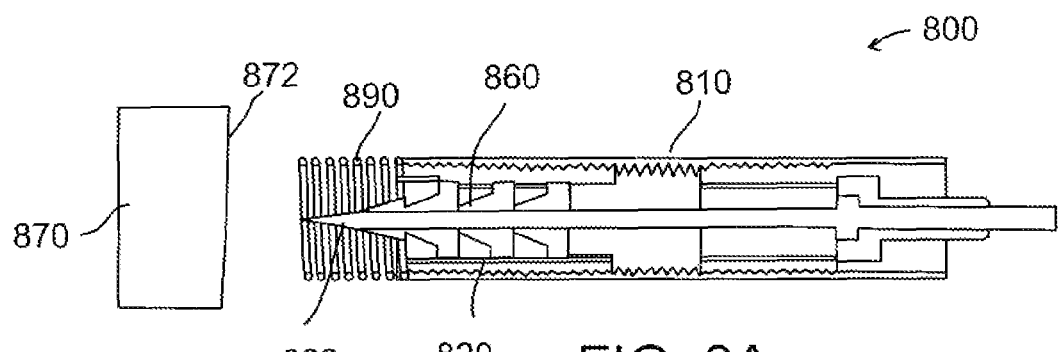
FIGS. 8A-8D are cross-sectional views of a fastening device having securing means in accordance with other embodiments of the invention.
Figure 8B:
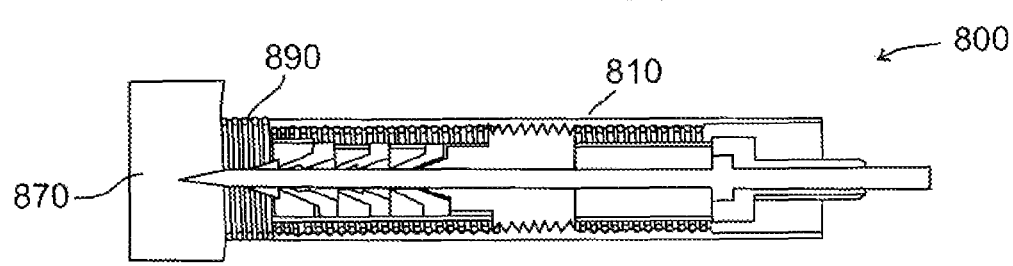
Figure 8C:
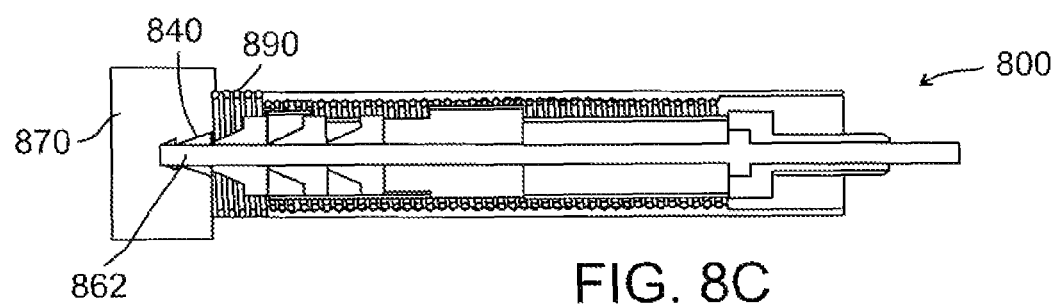
Figure 8D:
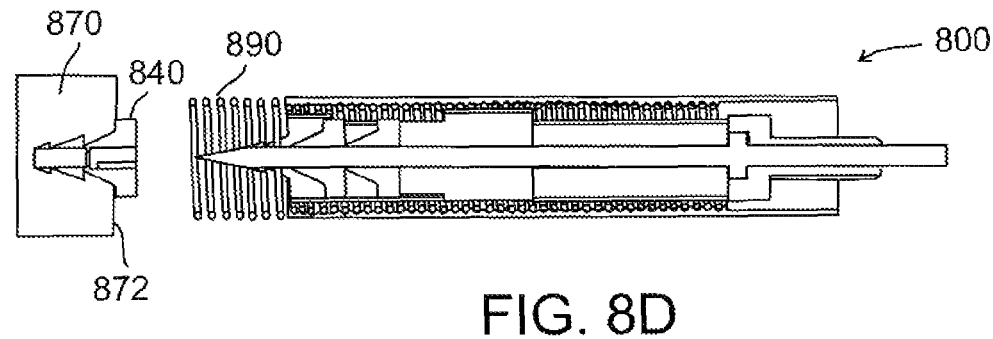

FIGS. 8A-8D are cross-sections of a fastening device 800 having different securing means in accordance with other embodiments of the invention. Fastening device 800 is similar to fastening device 500 described with respect to FIG. 5, except that it has a spring 890 at the distal end of outer tube 810. Spring 890 surrounds end 862 of needle 860 exposing out of inner tube 820. When device 800 is pushed against body tissue 870 as shown in FIG. 8B, spring 890 retracts, thereby exposing needle end 862. FIGS. 8C and 8D show how a fastener 840 is advanced over needle end 862, through mesh 872 and into body tissue 870.

Figure 8E:
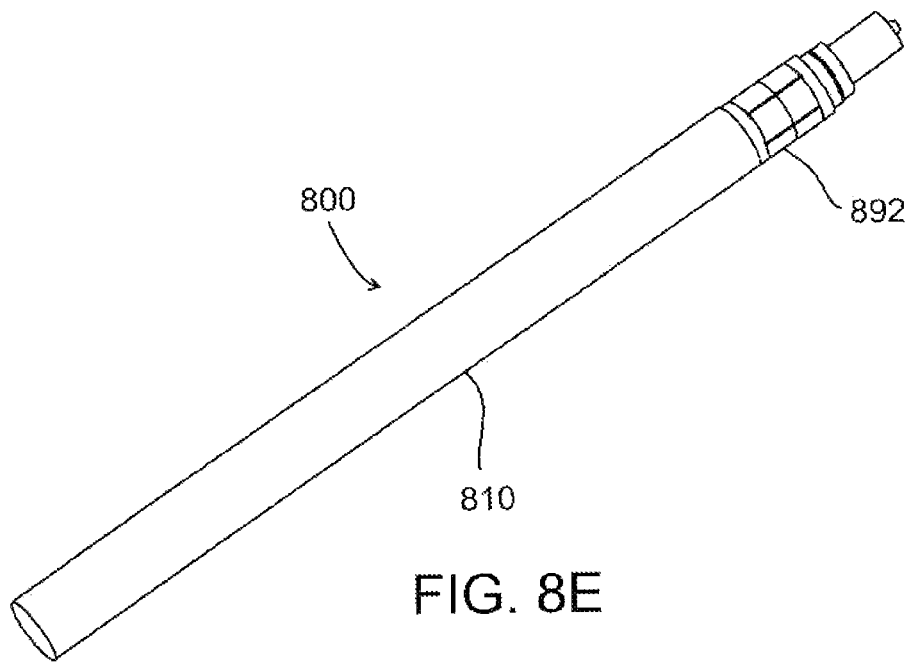
FIGS. 8E and 8F are schematic illustrations of a fastening device having securing means in accordance with yet other embodiments of the invention.
Figure 8F:
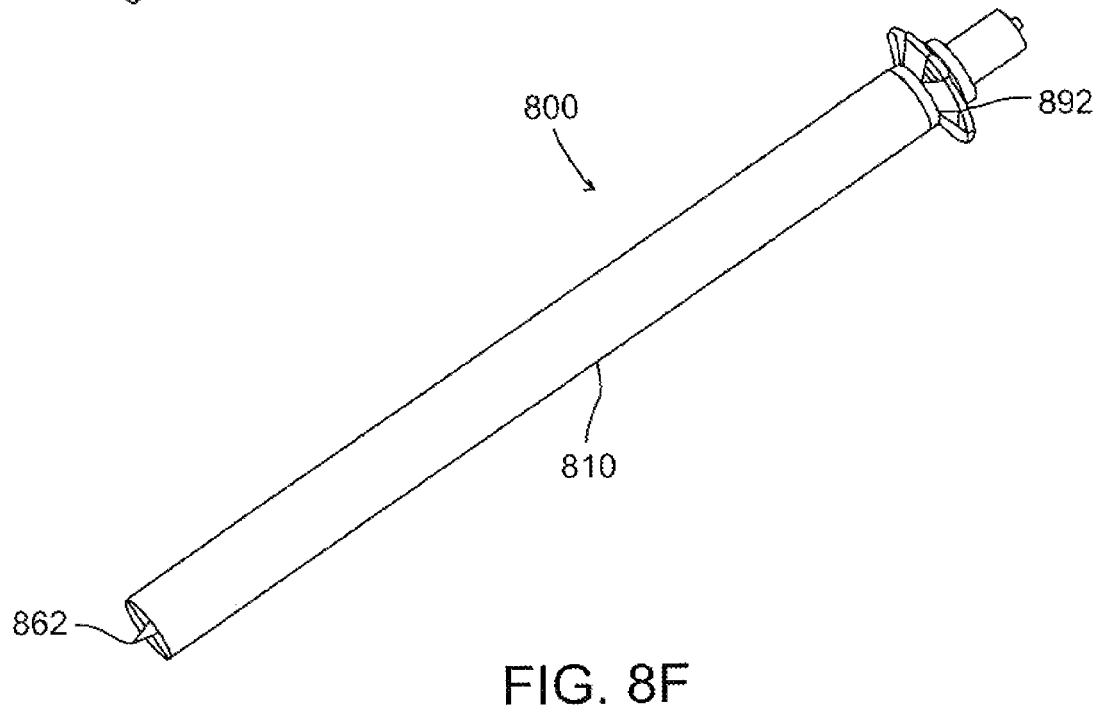

In some embodiments, spring 890 is replaced with a collapsible spring element 892 positioned at the proximal end of outer tube 810, as shown in FIGS. 8E and 8F. FIG. 8F shows spring like element 892 in retracted form, where needle end 862 is exposed.

In the embodiments of FIGS. 8A-8D, needle 860 can be either hollow or solid. Needle ends 762 and 862 may have any shape known in the art according to embodiments of the present invention.

In some embodiments of the invention, an attachment mechanism is provided for temporarily attaching the fastening device to body tissue. The attachment mechanism can reduce the linear force required to be applied by the fastening device and/or may align the fastening device with the tissue so that the fasteners will pierce tissue wall while being substantially perpendicular thereto.

Figure 9A:
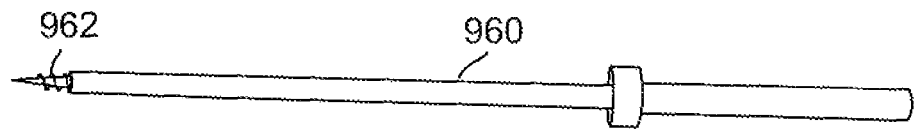
FIG. 9A is a schematic illustration of an attachment mechanism in accordance with some embodiments of the invention.

FIG. 9A illustrates a needle 960 to be used with any of the fastening device described in accordance with an embodiment of the present invention. Needle 960 comprises a threaded needle end 962 acting as attachment mechanism. Needle end 962 may be threaded into body tissue, thereby drawing the body tissue closer towards the distal end of the device while the device aligns with the tissue. The fasteners can then more easily be pierced and/or threaded into the body tissue.

Figure 9B:
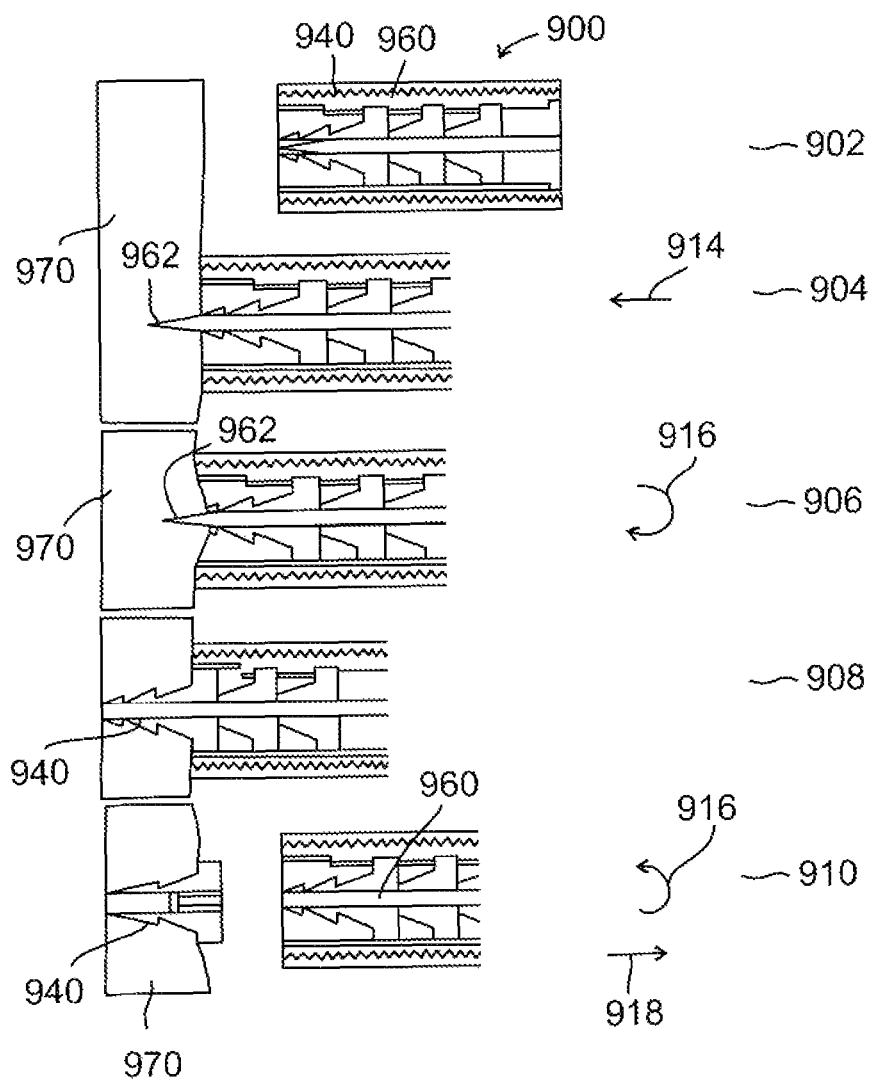
FIG. 9B are cross-sectional views illustrating a distal end of a fastening device incorporating the attachment mechanism of FIG. 9A during the stages of attaching the attachment mechanism to the body and piercing a fastener into the body tissue in accordance with some exemplary embodiments of the invention.

FIG. 9B are cross-sectional views illustrating a distal end of a fastening device 900 using needle 960 having threaded needle end 962 during the stages of attaching the attachment mechanism to the body and piercing a fastener 940 into body tissue 970 in accordance with some exemplary embodiments of the invention.

At 902 device 900 is introduced into a body of a living being and brought in proximity to body tissue 970. Device 900 is then pushed against body tissue 970 at 904 and needle 960 is advanced linearly with respect to device 900 in the direction 914 and pierced into body tissue 970. At 906, needle 960 is rotated in the direction 916, thereby pulling body tissue 970 towards device 900, thereby stabilizing the position and direction of device 900 with respect to body tissue 970. At 908 fastener is pushed into body tissue, either during rotation or not. At 910 the needle is rotated backwards in the direction 919 and retracted backwards in the direction 918 to release from body tissue 970. Device 900 is then moved to introduce another fastener into the body tissue or released from the body.

FIGS. 10A-10E illustrate an attachment mechanism in the form of thin wires in accordance with exemplary embodiment of the invention.

Figures 10A, 10B, 10C:
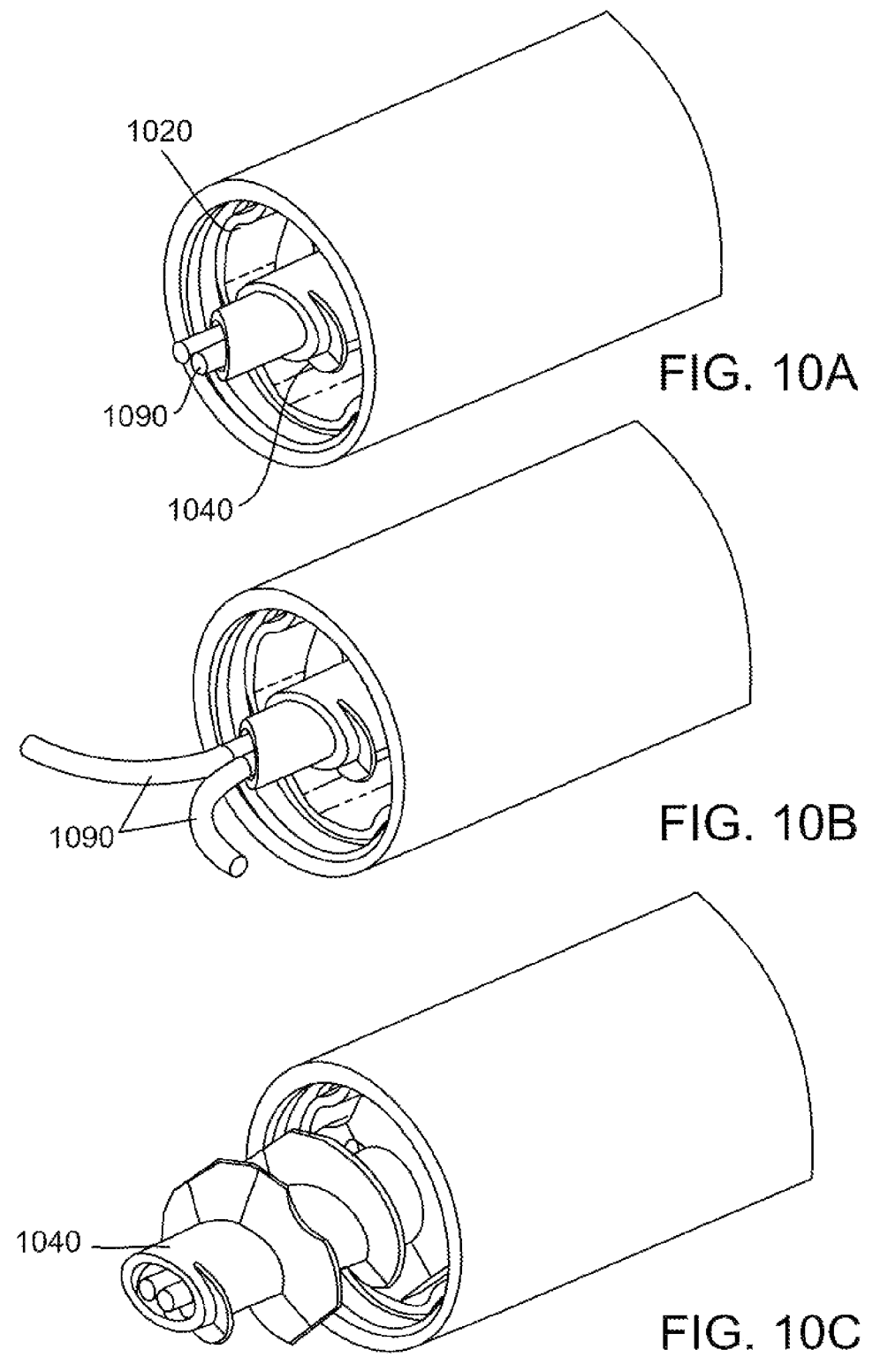

FIGS. 10A-10C are schematic illustrations of a distal section of fastening device in accordance with any of the embodiments described herein. Thin wires 1090 are provided through hollow fastener 1040 (and through a hollow shaft if provided) in inner tube 1020. Wires 1090 have a relaxed curved shape and are forced straight in hollow fasteners 1040. When the fastening device is brought close to body tissue, wires 1090 are pushed out of inner tube 1020 and into body tissue. When advanced out of the device, the distal ends of the wires return to their relaxed curved shape and are firmly clamped into the body tissue as shown in FIG. 10B, thereby drawing the tissue closer to the distal end of the fastening device and/or aligning the fastening device with the tissue. When fastener 1040 is advanced out of tube 1020, the wires are forced back to a straight shape.

Figure 10D:
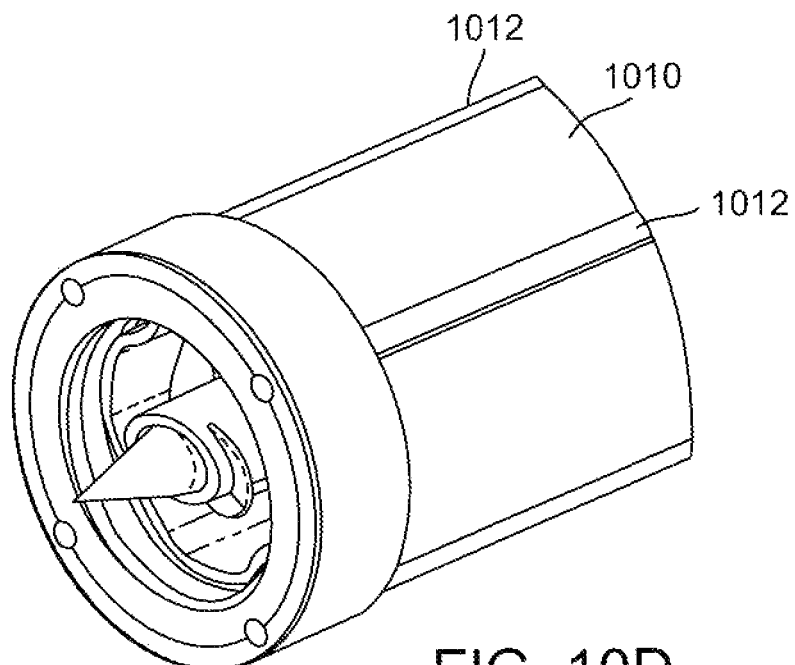
Figure 10E:
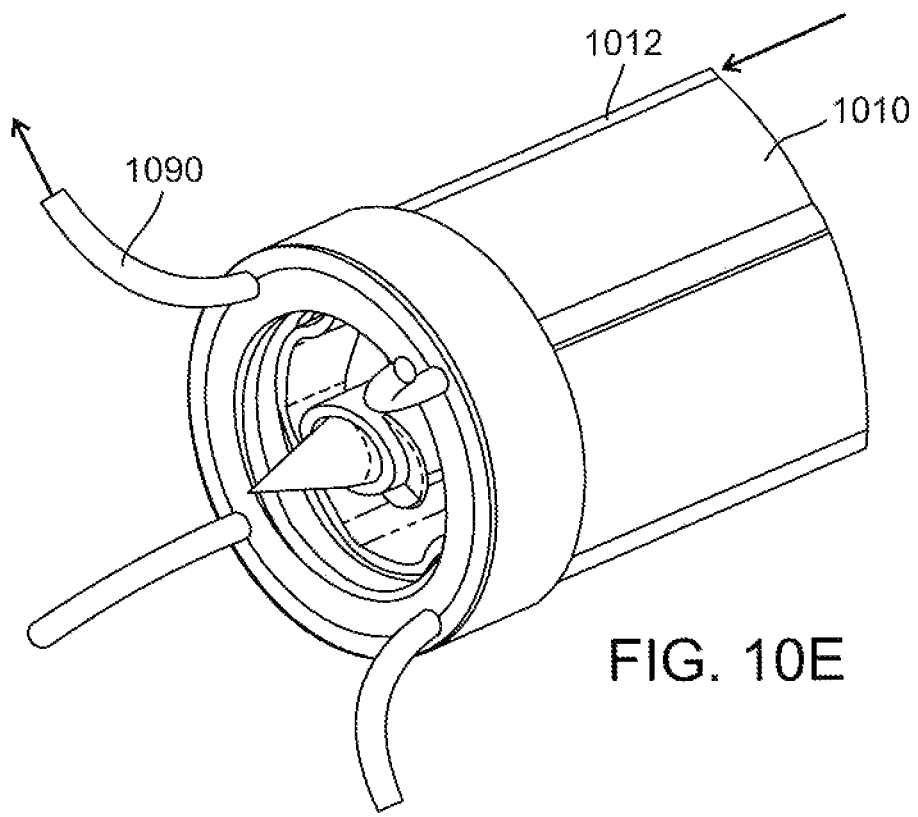

FIGS. 10D and 10E illustrate another embodiment of the invention where wires 1090 are threaded through conduits 1012 in outer tube 1010. As shown in FIG. 10E, when wires 1090 are pushed out of outer tube 1010, the wires return to their relaxed curved shape and are clamped into body tissue thereby drawing the tissue closer to the distal end of the fastening device and/or aligning the fastening device with the tissue.

In some embodiments, two wires are provided. Alternatively, any other number of wires can be provided, for example 3, 4, 5, 6, 8 or 10 wires.

The wires are preferably made of a material that is elastic and comprises a relaxed curved shape. Optionally, the wires have a diameter of between 0.2-1.5 mm. Optionally, the wires are of nickel titanium alloy.

In some embodiments of the invention, the surgical fastening device comprises means for preventing unintentional dislodging of the fasteners from the inner tube.

Figure 11A:
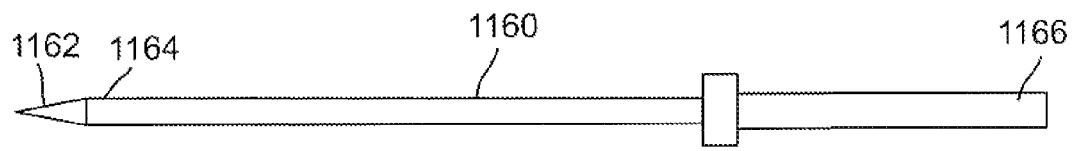
FIGS. 11A and 11B are schematic illustrations of the piercing part of the device in accordance with some embodiments of the invention.
Figure 11B:
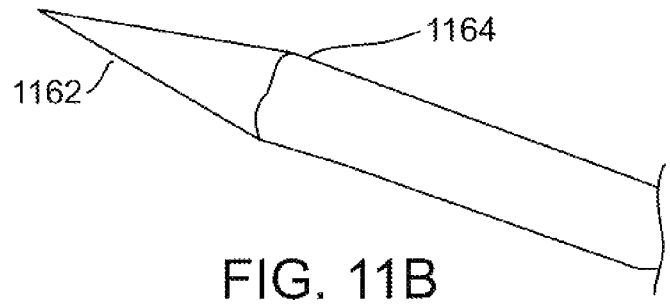

FIG. 11A illustrates an exemplary embodiment where a shaft 1160 on which the fasteners are fitted is provided. Shaft 1160 comprises a distal end 1164 located at the distal end of the device and a proximal end 1166 located at the proximal end of the device. Distal end 1164 of the shaft is broader than proximal end 1166, requiring that some force be exerted on a fastener in order for the fastener to pass over broader shaft end 1164. FIG. 11B is an enlarged view of distal end 1164. Optionally, distal end 1164 comprises a cross section substantially similar to the diameter of the bores of the fasteners, for example differing in about 0.01-0.1 mm as the diameter of the fasteners. Optionally, shaft 1160 also comprises a sharpened edge 1162 at its distal end for penetrating into body tissue. Sharpened edge 1162 is provided distal to broadened edge 1164.

Figure 12:
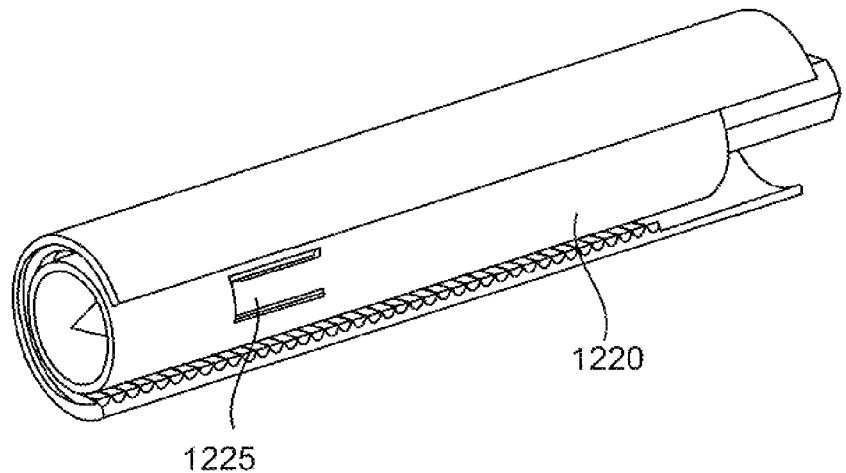
FIG. 12 is a schematic illustration of means for preventing unintentional dislodging of the fasteners from an inner tube of a fastening device in accordance with other embodiments of the invention.

FIG. 12 illustrates another embodiment where a protrusion or a lip 1225 is provided near the proximal end at the inner side of inner tube 1220, adapted to hold the distal most fastener and prevent its unintentional dislodging.

Figure 13A:
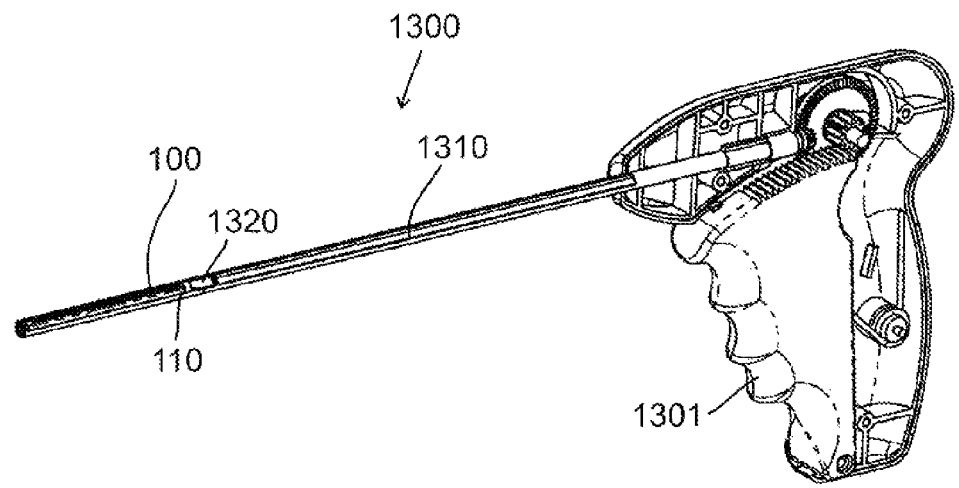
FIGS. 13A and 13B are partially cross-sectional views of a fastening device according to some embodiments of the invention embodied in a straight distal section of a surgical device.
Figure 13B:
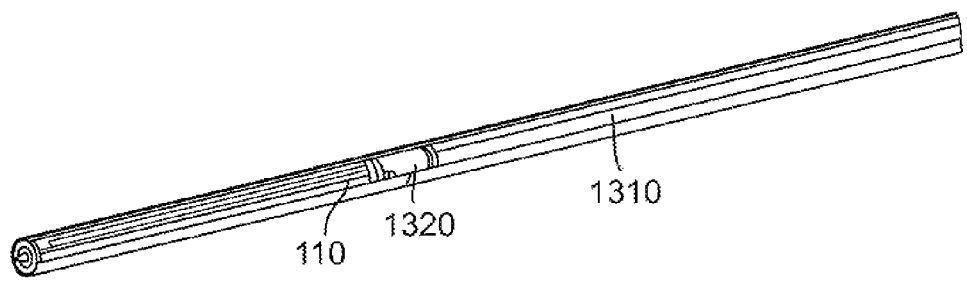

FIGS. 13A and 13B illustrate the fastening device 100 as shown in FIG. 1 embodied in a straight distal section of a surgical device 1300. Fastening device 100 may include any of the embodiments shown in FIGS. 2-12. Device 1300 includes a handle 1301, optionally a Covidien handle at its proximal section for rotating a shaft 1310 which is attached by a connector 1320 to inner tube 110. Optionally, connector 1320 houses proximal section 122 of the inner tube. Alternatively, connector 1320 and proximal section 122 of the inner tube are the same element. Where a non-static shaft or needle is provided on which the fasteners are fitted, as shown in FIG. 5 for example, a separate drive mechanism is provided within hollow shaft 1310 and hollow connector 1320, as known in the art.

Figure 14A:
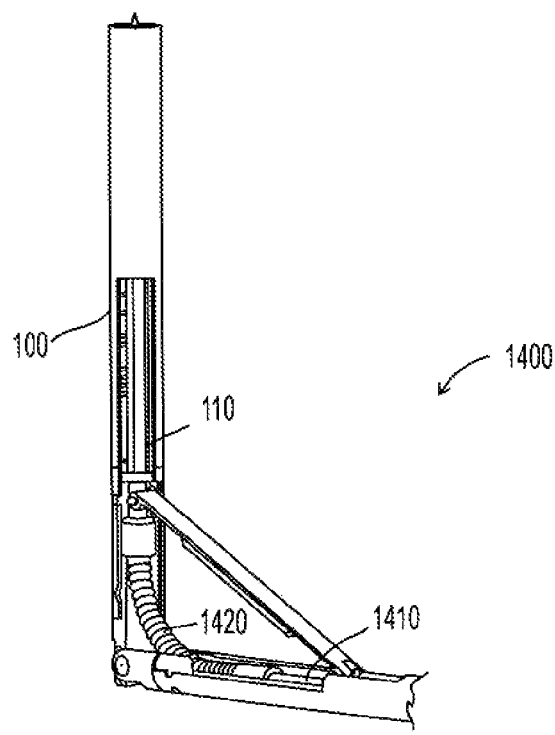
FIGS. 14A and 14B are partially cross-sectional views of a fastening device according to some embodiments of the invention embodied in a straight distal section of a surgical device.
Figure 14B:
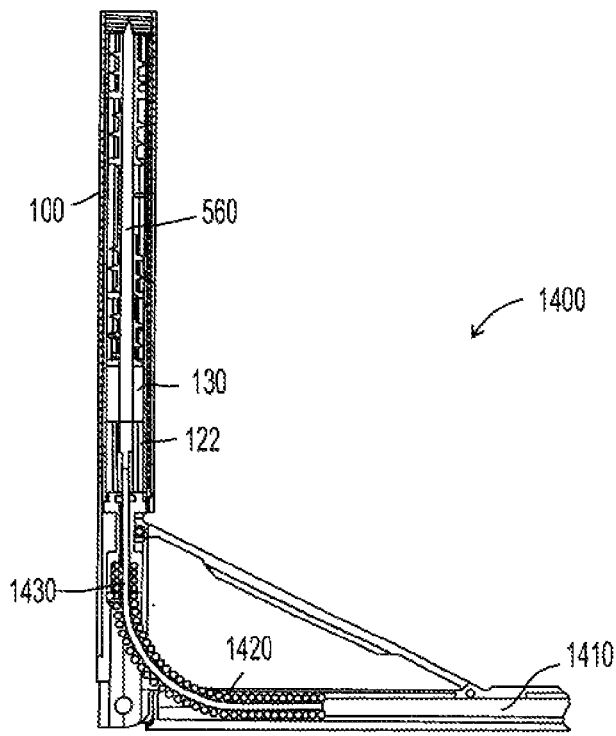

FIGS. 14A and 14B illustrate the fastening device 100 as shown in FIG. 1 embodied in an articulated distal section of a surgical device 1400. Fastening device 100 may include any of the embodiments shown in FIGS. 2-12. Surgical device 1400 may be any articulation device known in the art, for example the articulation devices described in WO2011/092692 by Sholev at al. incorporated herein by reference.

Device 1400 includes a handle (not shown) at its proximal section for rotating a shaft 1410 which is attached by an articulated flexible connector 1420 to proximal section 122 of inner tube 110. FIG. 14B shows an optional needle 560. Needle 560 may be static and connected to proximal section 122, or, as shown in FIG. 14 B, needle 560 may be driven by a flexible shaft 1430. The drive of shaft 1410 and 1430 are optionally independently of each other.

The embodiments described comprise a fixed internally threaded outer tube and a rotated non-threaded inner tube. In accordance with embodiments of the present invention, the rotated inner tube may be internally threaded while the outer tube may have a smooth inner surface. Optionally, fastener rotation is provided by having the fasteners ride on a shaft which has a cross-section which is not circular and which matches the fastener geometry. In these embodiments, the advancing element may or may not have wings but does not extend out of the inner tube, which may be provided without slots.

As used herein the term "about" refers to ±10%

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof. Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A fastening device comprising:
    an inner tube comprising a proximal end and a distal end, the inner tube adapted to receive one or more fasteners;
    an advancing element which converts rotational motion of the inner tube to linear pushing force on said one or more fasteners towards the distal end of the inner tube,
    wherein the inner tube is loadable with at least one fastener which does not rotate during linear advancement,
    wherein at least one fastener of said fasteners has a geometry which matches the geometry of the inner tube so that it rotates with the inner tube during linear advancement.

2. A fastening device according to claim 1, wherein the inner tube is adapted to rotate along its axis and provide said rotational motion to said advancing element.

3. A fastening device according to claim 1, wherein,
    said one or more fasteners comprises at least two fasteners which are positioned within the inner tube and adapted to advance linearly towards the distal end of the inner tube, wherein the at least two fasteners are adapted to rotate at different rates during linear advancement.

4. A fastening device according to claim 1, wherein the inner tube is loadable with at least one fastener which rotates during linear advancement and at least one fastener which does not rotate during linear advancement at the same time.

5. A fastening device according to claim 1, wherein the inner tube is connected to a rotary drive mechanism of a surgical device.

6. A fastening device according to claim 1, wherein at least two of said fasteners comprise interlocking elements adapted to connect the at least two fasteners to each other such that the connected fasteners will rotate together.

7. A fastening device according to claim 1, wherein the inner tube has a non-circular shaped cross-section and wherein at least one of said fasteners comprises a non-circular shaped base having at least one common plane with the non-circular cross-section.

8. A fastening device according to claim 1, wherein the fastening device is embodied in at least one of a straight distal section of a surgical device and a distal section of an articulating surgical device.

9. A fastening device according to claim 1, wherein at least one of said fasteners is threaded and wherein a pitch of a thread to said threaded fastener provides linear movement when engaging tissue that is greater than provided by said linear pushing force.

10. A fastening device according to claim 1, wherein at least one of said fasteners is threaded and wherein the pitch of the thread to said threaded fastener provides linear movement when engaging tissue that matches that provided by said linear pushing force.

11. A fastening device according to claim 1, wherein the fastening device further comprises an outer tube into which the inner tube is inserted, and wherein the outer tube is static and does not move with respect to other elements at the distal end of the device.

12. A fastening device according to claim 1, wherein said fastening device is adapted to be introduced into a body and wherein said one or more fasteners comprises a plurality of fasteners which can be introduced into said body without having to remove said fastening device out of the body.

13. A fastening device according to claim 1, wherein the inner tube comprises at least one longitudinal slot along at least a portion of its length, the device comprising an internally threaded outer tube into which the inner tube is inserted,
wherein said advancing element comprises at least one wing, the advancing element positioned within the inner tube such that the threads of the at least one wing protrude out of the at least one slot and are threaded in the inner threads of the outer tube; and wherein said one or more fasteners are positioned within the inner tube between the advancing element and the distal end of the inner tube;
wherein rotation of the inner tube causes the threaded wing to advance along the inner threads of the outer tube and thereby to advance the advancing element and the fasteners linearly towards the distal end of the inner tube.

14. A fastening device according to claim 13, wherein the outer tube does not move linearly with respect to the inner tube.

15. A fastening device according to claim 1, wherein the fasteners comprise a base and a piercing element and wherein at least one fastener comprises a cavity in its base for receiving a piercing element of another fastener.

16. A fastening device according to claim 15, wherein both the base and the piercing element of said fasteners are introduced into the body by said rotational movement.

17. A fastening device according to claim 1, wherein the device further comprises a shaft on which the fasteners are fitted and wherein the movement of the shaft is independent of the movement of the fasteners.

18. A fastening device according to claim 17, wherein the shaft comprises a sharpened distal end for piercing into body tissue and wherein the shaft is hollow and includes an inner shaft for protecting the sharpened end from harming body tissue, wherein the inner shaft is adapted to be pushed into the sharpened shaft when pushed against body tissue, thereby revealing the sharpened end.

19. A fastening device according to claim 17, wherein the shaft is adapted to move in a linear direction only.

20. A fastening device according to claim 17, wherein the shaft comprises a threaded end.

21. A fastening device according to claim 17, wherein the shaft comprises a broadened distal end to prevent unintentional dislodgement of the fasteners from the shaft.

22. A fastening device according to claim 1, wherein the inner tube has a circular shaped cross-section with a non-constant diameter and wherein at least one fastener of said fasteners comprises a circular shaped base having a non-constant diameter fitted to said inner tube.

23. A fastening device according to claim 22, wherein said circular shaped cross-section with a non-constant diameter contains a flat or nearly flat side.

24. A method of advancing a fastener, the method comprising:
introducing a fastening device into a body, the device including an outer tube into which an inner tube is inserted, the inner and outer tube including a distal end and a proximal end and a first set of fasteners including one or more fasteners positioned in the inner tube;
providing a rotational movement to the inner tube; and
converting said rotational movement into a linear pushing force on said fasteners and linearly advancing said fasteners in the inner tube towards the distal end of the inner tube,
wherein at least one of said fasteners has a geometry which matches the geometry of the inner tube so that it rotates with the inner tube during linear advancement, and
wherein the outer tube is static and does not move with respect to other elements at the distal end of the device.

25. A method according to claim 24, wherein at least one additional fastener of said fasteners has a threaded piercing portion and wherein the method further comprises:
rotating the inner tube thereby linearly advancing the additional fastener in the inner tube and out of the inner tube and rotating the threaded portion into body tissue.

26. A method according to claim 24, wherein providing a rotational movement further comprises rotating an advancing element positioned within the inner tube and comprising at least one threaded wing extending out of at least one slot of the inner tube, such that the threaded wing is threaded into inner threads of an outer tube in which the inner tube is positioned, thereby linearly advancing the advancing element within the inner tube and advancing the fasteners by pushing thereon by the rotating advancing element.

27. A method according to claim 24, further comprising:
threading a threaded end of a shaft into body tissue.

28. A method according to claim 24, wherein said device is provided in contact with a body tissue and wherein said advancing comprises advancing said one or more fasteners into said body tissue.

29. A method according to claim 24, wherein said one or more fasteners comprises a plurality of fasteners which can be introduced into said body without having to remove said fastening device out of the body.

30. A method according to claim 24, wherein the fasteners comprise a base and a piercing element,
- wherein at least one fastener comprises a cavity in its base for receiving a piercing element of another fastener, and
- wherein both the base and the piercing element of said fasteners are introduced into the body by said rotational movement.

* * * * *